(12) United States Patent
Arnold

(10) Patent No.: US 10,610,526 B2
(45) Date of Patent: Apr. 7, 2020

(54) NICOTINE REPLACEMENT THERAPY PRODUCTS COMPRISING SYNTHETIC NICOTINE

(71) Applicant: Next Generation Labs, LLC, San Diego, CA (US)

(72) Inventor: Michael Arnold, San Diego, CA (US)

(73) Assignee: NEXT GENERATION LABS, LLC, San Diego, CA (US)

( * ) Notice: Subject to any disclaimer, the term of this patent is extended or adjusted under 35 U.S.C. 154(b) by 0 days.

(21) Appl. No.: 15/396,274

(22) Filed: Dec. 30, 2016

(65) Prior Publication Data

US 2017/0189388 A1    Jul. 6, 2017

Related U.S. Application Data

(60) Provisional application No. 62/273,296, filed on Dec. 30, 2015.

(51) Int. Cl.
| | |
|---|---|
| *A61K 31/465* | (2006.01) |
| *A61P 25/34* | (2006.01) |
| *A24F 47/00* | (2020.01) |
| *A61K 9/68* | (2006.01) |
| *A61K 9/00* | (2006.01) |
| *A61K 9/70* | (2006.01) |
| *C07D 401/04* | (2006.01) |
| *A61M 11/00* | (2006.01) |

(52) U.S. Cl.
CPC .......... *A61K 31/465* (2013.01); *A24F 47/002* (2013.01); *A61K 9/006* (2013.01); *A61K 9/0058* (2013.01); *A61K 9/7023* (2013.01); *A61P 25/34* (2018.01); *C07D 401/04* (2013.01); *A61M 11/00* (2013.01)

(58) Field of Classification Search
None
See application file for complete search history.

(56) References Cited

U.S. PATENT DOCUMENTS

| | | | | |
|---|---|---|---|---|
| 4,597,961 A * | 7/1986 | Etscorn | ........... | A61K 9/7084 424/448 |
| 4,943,435 A * | 7/1990 | Baker | ........... | A61K 9/7053 131/335 |
| 5,227,391 A | 7/1993 | Caldwell et al. | | |
| 5,593,684 A | 1/1997 | Baker | | |
| 6,344,222 B1 * | 2/2002 | Cherukuri | ........... | A61K 9/0058 424/440 |
| 6,645,470 B1 * | 11/2003 | Reynolds | ........... | A61K 31/465 206/534 |
| 6,709,671 B2 * | 3/2004 | Zerbe | ........... | A61K 8/0208 424/435 |
| 6,881,738 B2 | 4/2005 | Buccafusco et al. | | |
| 7,832,410 B2 | 11/2010 | Hon | | |
| 8,367,837 B2 | 2/2013 | Divi et al. | | |
| 8,378,110 B1 | 2/2013 | Divi et al. | | |
| 8,389,733 B2 | 3/2013 | Divi et al. | | |
| 9,556,142 B2 * | 1/2017 | Arnold | ........... | C07D 401/04 |
| 2003/0082109 A1 * | 5/2003 | Gorenstein | ........... | A61K 9/0058 424/48 |
| 2004/0002520 A1 * | 1/2004 | Soderlund | ........... | A61K 9/006 514/343 |
| 2011/0268809 A1 | 11/2011 | Brinkley et al. | | |
| 2012/0197022 A1 | 8/2012 | Divi et al. | | |
| 2014/0031554 A1 * | 1/2014 | Tian | ........... | C07D 401/04 546/278.4 |
| 2014/0345631 A1 | 11/2014 | Bowen et al. | | |
| 2015/0024012 A1 * | 1/2015 | Grossman | ........... | A61K 9/006 424/400 |
| 2015/0098996 A1 | 4/2015 | Gao | | |

FOREIGN PATENT DOCUMENTS

EP        2487172 A1    8/2012

OTHER PUBLICATIONS

Carmella et al. "Evidence for Endogenous Formation of Tobacco-Specific Nitrosamines in Rats Treated with Tobacco Alkaloids and Sodium Nitrite". Carcinogenesis, 1997; 18(3):587-592. (Year: 1997).*
Hukkanen et al. "Metabolism and Disposition Kinetics of Nicotine". Pharmacological Reviews. 2005; 57(1):79-115. (Year: 2005).*
West R. "The Deadly Weed: Nicotine and Tobacco Dependence". The Biochemist. 2002. pp. 15-17. (Year: 2002).*
Nordberg A. "A Comparison of the (S)(-) and (R)(+) Enantiomers of Nicotine with Respect to Pharmacological and Behavioral Effects and Receptor Binding Properties in Experimental Animal and Man". Med Chem Res. 1993; 2:522-529. (Year: 1993).*
Billen et al. "Molecular Actions of Smoking Cessation Drugs at Alpha4Beta2 Nicotinic Receptors Defined in Crystal Structures of a Homologous Binding Protein". PNAS. Jun. 5, 2012; 109(23):9173-9178. (Year: 2012).*
International Search Report and Written Opinion of the International Searching Authority dated Mar. 10, 2017, issued in corresponding PCT/US2016/069593, 8 pages.
International Search Report dated Jan. 3, 2017, issued in corresponding International Application No. PCT/US2016/058544, 2 pages.

(Continued)

*Primary Examiner* — Leslie A. Royds Draper
(74) *Attorney, Agent, or Firm* — Lewis Roca Rothgerber Christie LLP

(57) ABSTRACT

A composition suitable for use in nicotine replacement therapy products includes a nicotine product that includes a synthetic nicotine that is substantially free of one or more contaminants and/or impurities normally associated with tobacco-derived nicotine. For example, the synthetic nicotine is substantially free of one or more of nicotine-1'-N-oxide, nicotyrine, nornicotyrine, 2',3-bipyridyl, cotinine, anabasine, and/or anatabine. The composition further comprises one or more pharmaceutically acceptable excipients, additives and/or carriers. The nicotine replacement therapy products may include any number of such products, including transdermal nicotine delivery patches, nicotine gums, synthetic chewing tobacco, synthetic snuff, and synthetic strips (e.g., dissolvable synthetic tobacco). Additionally, a method of treating nicotine addiction includes administering a nicotine replacement composition, e.g., via a nicotine replacement therapy product, to a user.

20 Claims, No Drawings

(56) References Cited

OTHER PUBLICATIONS

Written Opinion dated Jan. 3, 2017, issued in International Application No. PCT/US2016/058544, 5 pages.
International Search Report dated Jun. 30, 2016, issued in International Application No. PCT/US2015/057017, 2 pages.
Written Opinion dated Jun. 30, 2016, issued in International Application No. PCT/US2015/057017, 3 pages.
Aceto et al., "Optically Pure (+)-Nicotine from (±) Nicotine and Biological Comparisons with (-)-Nicotine", *Journal of Medicinal Chemistry*, 1979, 22(2):174-177.
Culp et al., "Determination of Synthetic Components in Flavors by Deuterium/Hydrogen Isotopic Ratios", *J. Agric. Food Chem.*, 1992, 40:1892-1897.
Culp et al., "Identification of Isotopically Manipulated Cinnamic Aldehyde and Benzaldehyde", *J. Agric. Food Chem.*, 1990, 38:1249-1255.
Detraglia et al., "Separation of D-(+)-Nicotine from a Racemic Mixture by Stereospecific Degradation of the L-(-) Isomer with *Pseudomonas putida*", *Applied and Environmental Microbiology*, May 1980, 39(5):1067-1069.
Fletouris et al., "Trace Analysis of Oxytetracycline and Tetracycline in Milk by High-Performance Liquid Chromatography", *J. Agric. Food Chem.*, 1990, 38:1913-1917.
Lloyd et al., "Pyrrolidine amides of pyrazolodihydropyrimidines as potent and selective Kv1.5 blockers", *Bioorganic & Medicinal Chemistry Letters*, 2010, 20:1436-1439.
Extended European Search Report dated Jul. 26, 2019, issued in corresponding EP Application No. 16882784.8, 7 pages.
Benowitz, Neal L., et al., "Nicotine Chemistry, Metabolism, Kinetics and Biomarkers", NIH Public Access, Author Manuscipt, 29 pages, 2009 (final published as Hanb Exp Pharmacol., 2009, vol. 192, pp. 29-60).
Hukkanen, Janne, et al., "Metabolism and Disposition Kinetics of Nicotine", Pharmacological Reviews, vol. 57, No. 1, 2005, pp. 80-115.
Thuerauf, Norbert, et al., "The Influence of Mecamylamine on Trigeminal and Olfactory Chemoreception of Nicotine", Neuropsychopharmacology (2006) 31, pp. 450-461.

\* cited by examiner

NICOTINE REPLACEMENT THERAPY PRODUCTS COMPRISING SYNTHETIC NICOTINE

CROSS-REFERENCE TO RELATED APPLICATION

This application claims priority to and the benefit of U.S. Provisional Application No. 62/273,296 filed Dec. 30, 2015, the entire content of which is incorporated herein by reference.

BACKGROUND

Nicotine Replacement Therapy (NRT) products are devices and compositions typically including strategically-dosed delivery forms of nicotine. The products are designed to aid the user in cessation of tobacco addiction. Many nicotine replacement therapy products include concentrations of nicotine designed to reduce the desire for tobacco products. Smoking cessation programs use these therapies to replace the physiologic need for nicotine from tobacco products while using other modalities to reduce the psychological desire to use tobacco products. The uses of NRT products vary from smoking cessation devices and compositions, to recreational compositions to enhance the user's recreational experience, or minimize socially-unwanted or illegal activities now associated with the smoking of tobacco in public.

The nicotine currently used in NRT products is typically tobacco-derived, i.e., extracted from tobacco leaves. The nicotine extract is isolated in its semi-pure form along with many contaminants. For example, a typical USP grade nicotine derived from tobacco often contains at least the following contaminants: Anabasine; Cotinine; Nornicotine; and Trans-3'-hydroxycotinine; as well as the known carcinogen, polyaromatic hydrocarbons. Many of these tobacco-derived nicotine contaminants have been shown to cause serious ailments for the human system, including cancer. Tobacco-derived nicotine, even when purified to levels compliant with the USP monograph for purity, retains many of these contaminants, and thus even highly-purified tobacco-derived nicotine can be problematic for the consumer. In addition, these contaminates contribute to a less-desirable consumer product, primarily due to foul taste and a malodorous characteristic of the products utilizing commercially available tobacco-derived nicotine extracts. These aspects of the tobacco-derived nicotine severely hamper the quality of NRT oral products such as sprays, strips, snuffs, chews, or gums. The contaminants, although sometimes in low concentrations, do get into the human system upon using traditional NRT products.

SUMMARY

According to embodiments of the present invention, a composition suitable for use in a nicotine replacement product includes a nicotine product comprising a synthetic nicotine substantially free of one or more of nicotine-1'-N-oxide, nicotyrine, nornicotyrine, cotinine, 2',3-bipyridyl, anabasine, N-methyl anatabine, N-methyl anabasine, anabasine, and/or anatabine. The composition further includes one or more pharmaceutically acceptable excipients, additives and/or carriers.

According to some embodiments, a nicotine replacement therapy product includes the nicotine replacement composition. In some embodiments, the nicotine replacement therapy product may further include an atomizer for atomizing the composition. According to some embodiments, the nicotine replacement therapy product may further include a matrix comprising a resin, a polymer or a gum base in which the nicotine replacement composition is embedded or impregnated, and a support on which the matrix and the composition are supported. In some embodiments, the nicotine replacement therapy product further includes a reservoir housing the composition, a support, and a permeable membrane. According to some embodiments, the nicotine replacement therapy product may further include a resin, a polymer or a gum base. The nicotine replacement therapy product may include the nicotine replacement composition impregnated or embedded in polymer particles or fibers. The polymer particles or fibers may be soluble in water and/or saliva.

According to some embodiments, a method of treating nicotine addiction includes administering the nicotine replacement composition to a user. The administering the nicotine replacement composition may include administering a first nicotine replacement composition having a first concentration of the nicotine product, and then administering a second nicotine replacement composition having a second concentration of the nicotine product, where the second concentration is lower than the first concentration. In some embodiments, the administering may include administering a first nicotine replacement composition having a first concentration of R-isomer in the nicotine product, and then administering a second nicotine replacement composition having a second concentration of R-isomer in the nicotine product, where the second concentration of R-isomer is greater than the first concentration of R-isomer.

DETAILED DESCRIPTION

According to embodiments of the present invention, a composition suitable for nicotine replacement therapy products (also referred to herein as "nicotine replacement compositions" or "NRT compositions") includes a nicotine product that includes a synthetic nicotine that is substantially free of certain contaminants or impurities normally found in tobacco-derived nicotine, such as for example nicotine-N'-oxide (e.g., nicotine-1'-N-oxide), nicotyrine (e.g., β-Nicotyrine), cotinine, nornicotyrine, 2',3-bipyridyl, anabasine, N-methyl anatabine, N-methyl anabasine, anabasine, and/or anatabine. As used herein, the term "substantially" is used as a term of approximation, and not as a term of degree, and is intended to account for the possibility of incidental impurities in the listed component. For example, the term "substantially free of" the listed compounds refers to a composition that does not include added amounts of the listed compounds, and refers to the inclusion of any such components in the composition only as incidental impurities in negligible amounts that do not contribute to the function or properties of the composition. In contrast, a composition that is "free of" or "completely free of" the listed compounds contains no measurable amount of the listed components.

In some embodiments, for example, the nicotine replacement composition may include a synthetic nicotine that is free or substantially free of any one or more of nicotine-N'-oxide (e.g., nicotine-1'-N-oxide), nicotyrine (e.g., β-Nicotyrine), cotinine, nornicotyrine, 2',3-bipyridyl, anabasine, N-methyl anatabine, N-methyl anabasine, anabasine, and/or anatabine. In some embodiments, the nicotine replacement composition may include a synthetic nicotine that is free or substantially free of any combination of two or more of nicotine-N'-oxide (e.g., nicotine-1'-N-oxide), nicotyrine (e.g., β-Nicotyrine), cotinine, nornicotyrine, 2',3-bipyridyl, anabasine, N-methyl anatabine, N-methyl anabasine, anabasine, and/or anatabine. In some embodiments, the nicotine replacement composition may include a synthetic nicotine that is free or substantially free of all of nicotine-N'-oxide (e.g., nicotine-1'-N-oxide), nicotyrine (e.g., β-Nicotyrine), cotinine, nornicotyrine, 2',3-bipyridyl, anabasine, N-methyl anatabine, N-methyl anabasine, anabasine, and/or anatabine.

According to aspects of embodiments of the present invention, a composition suitable for nicotine replacement therapy products (also referred to herein as "nicotine replacement compositions" or "NRT compositions") comprises a nicotine product comprising a synthetic nicotine that is free or substantially free of nicotyrine (e.g., β-Nicotyrine), cotinine, nornicotyrine, 2',3-bipyridyl, anabasine, N-methyl anatabine, N-methyl anabasine, anabasine, and/or anatabine. In some embodiments, for example, the nicotine replacement composition may include a synthetic nicotine that is free or substantially free of any one or more of nicotyrine (e.g., β-Nicotyrine), cotinine, nornicotyrine, 2',3-bipyridyl, anabasine, N-methyl anatabine, N-methyl anabasine, anabasine, and/or anatabine. In some embodiments, the nicotine replacement composition may include a synthetic nicotine that is free or substantially free of any combination of two or more of nicotyrine (e.g., β-Nicotyrine), cotinine, nornicotyrine, 2',3-bipyridyl, anabasine, N-methyl anatabine, N-methyl anabasine, anabasine, and/or anatabine. In some embodiments, the nicotine replacement composition may include a synthetic nicotine that is free or substantially free of all of nicotyrine (e.g., β-Nicotyrine), cotinine, nornicotyrine, 2',3-bipyridyl, anabasine, N-methyl anatabine, N-methyl anabasine, anabasine, and/or anatabine.

For example, in some embodiments, a nicotine replacement composition or NRT composition comprises a nicotine product comprising a synthetic nicotine that is free or substantially free of nicotyrine (e.g., β-Nicotyrine), cotinine, anabasine, N-methyl anatabine, N-methyl anabasine, anabasine, and/or anatabine. In some embodiments, for example, the nicotine replacement composition may include a synthetic nicotine that is free or substantially free of any one or more of nicotyrine (e.g., β-Nicotyrine), cotinine, anabasine, N-methyl anatabine, N-methyl anabasine, anabasine, and/or anatabine. In some embodiments, the nicotine replacement composition may include a synthetic nicotine that is free or substantially free of any combination of two or more of nicotyrine (e.g., β-Nicotyrine), cotinine, anabasine, N-methyl anatabine, N-methyl anabasine, anabasine, and/or anatabine. In some embodiments, the nicotine replacement composition may include a synthetic nicotine that is free or substantially free of all of nicotyrine (e.g., β-Nicotyrine), cotinine, anabasine, N-methyl anatabine, N-methyl anabasine, anabasine, and/or anatabine.

In some embodiments, for example, a nicotine replacement composition or NRT composition comprises a nicotine product comprising a synthetic nicotine that is free or substantially free of anabasine, N-methyl anatabine, N-methyl anabasine, cotinine and/or anatabine. In some embodiments, for example, the nicotine replacement composition may include a synthetic nicotine that is free or substantially free of one or more of anabasine, N-methyl anatabine, N-methyl anabasine, cotinine, and/or anatabine. In some embodiments, the nicotine replacement composition may include a synthetic nicotine that is free or substantially free of two or more of anabasine, N-methyl anatabine, N-methyl anabasine, cotinine and/or anatabine. For example, in some embodiments, the nicotine replacement composition may include a synthetic nicotine that is free or substantially free of two or more of anabasine, N-methyl anatabine, N-methyl anabasine, cotinine and/or anatabine.

Those of ordinary skill in the art would understand known methods of determining the presence of the compounds and impurities discussed herein. However, one nonlimiting example of a suitable technique for determining whether these impurities are present in a particular composition includes USP-HPLC, i.e., high performance liquid chromatography according to USP standards, which tests for the main impurities in tobacco-derived or natural nicotine (including, e.g., cotinine and anatabine). Those of ordinary skill in the art would be readily capable of performing such a technique, and would recognize a yield of a detectable amount of any of the impurities or contaminants found in tobacco-derived nicotine confirms the composition as natural or tobacco-derived nicotine.

The synthetic nicotine according to embodiments of the present invention is distinct and distinguishable from its tobacco-derived or natural counterpart. The impurities discussed above are one way in which the synthetic nicotine according to embodiments of the present invention may be chemically and physically distinguished from tobacco-derived or natural nicotine. However, additional methods for distinguishing synthetic vs. natural nicotine may also be used. For example, because natural nicotine is derived from, or extracted from a living tobacco plant, the nicotine obtained from that source will inherently include a measurable amount of radioactive isotopes, e.g., $^{14}C$, $^{13}C$ and D. See Randolph A. Culp et al., "Identification of Isotopically Manipulated Cinnamic Aldehyde and Benzaldehyde," *J. Agric. Food Chem.,* 1990, 38, 1249-1255; and Randolph A. Culp et al., "Determination of Synthetic Components in Flavors by Deuterium/Hydrogen Isotopic Ratios," referred to collectively herein as "the Culp references," the entire contents of both of which are incorporated herein by reference. As noted in the Culp references, a natural (or plant-derived) source of a compound can be determined through isotopic analysis to determine the level of $^{14}C$ as well as the isotopic abundance of $^{13}C$ and D (typically reported as $\delta^{13}C$ and OD, respectively). The $\delta^{13}C$ and $\delta D$ indications refer to the isotopic abundance, i.e., the ratio of the heavier isotope (e.g., $^{13}C$ or D) to the lighter isotope (e.g., $^{12}C$ or H). As discussed in the Culp references, these ratios are measurably different in corresponding synthetic vs. naturally-derived or plant-derived compounds. As such, in some embodiments of the present invention, the synthetic nicotine has an isotopic abundance (e.g., a $\delta^{13}C$ and $\delta D$ value) and/or $^{14}C$ level that is different from that of the natural or tobacco-derived counterpart compound. For example, in some embodiments, the synthetic nicotine has an isotopic abundance (e.g., a $\delta^{13}C$ and $\delta D$ value) and/or $^{14}C$ level that is lower than that of the natural or tobacco-derived counterpart compound. For example, in some embodiments, the synthetic nicotine may have a $^{14}C$ level of up to about 10 dpm/gC (disintegrations per minute/grams C). In some embodiments, for example the synthetic nicotine may have $^{14}C$ level of about 0.1 to about 9 dpm/gC, or in some embodiments about 2 to about 8 dpm/gC, or about 3 to about 8 dpm/gC. For example, in some embodiments, the synthetic nicotine may have a $^{14}C$ level of about 3.5 to about 7 dpm/gC, or about 4 to about 6 dpm/gC. In contrast, the 2015 and present day $^{14}C$ reference standard is 14.0 dpm/gC. Accordingly, the synthetic nicotine according to embodiments of the present invention has a significantly different $^{14}C$ level than that of natural nicotine (i.e., based on the 2015 and present day reference standard for $^{14}C$ activity). For example, in some embodiments, the synthetic nicotine has a $^{14}C$ level that is up to about 72% that of natural nicotine, or about 0.5% to about 65% that of natural nicotine. In some embodiments, for example, the synthetic nicotine has a $^{14}C$ level that is about 14% to about 58% that of natural nicotine, or about 20% to about 58% that of natural nicotine. For example, in some embodiments, the synthetic nicotine has a $^{14}C$ level that is about 25% to about 50% that of natural nicotine, or about 28% to about 43% that of natural nicotine.

As referenced above, the unstable radio-isotope of carbon, $^{14}C$, has different radioactivity based on its age, e.g., the older it is, the less radioactive it becomes. Comparison of the radioactivity of natural or tobacco-derived nicotine (e.g., the United States Pharmacopeia (USP) standard) to that of a synthetic sample provides an avenue for identifying the source of the nicotine. For example, if the nicotine is petroleum based, then the radioactivity will be significantly lower than if the nicotine is natural or tobacco-derived. However, some synthetic nicotine may be produced from chemicals that originate from living plants, e.g., sugar cane or corn. To tell the difference between tobacco-derived nicotine and such sugar- or corn-derived nicotine, the amounts of the stable isotope of carbon are determined. Since sugar cane and corn are in a different class of plant than tobacco, they metabolize the heavy isotopes of carbon ($C^{13}$) and water ($D_2O$) at different magnitudes than the tobacco plant. As such, if the comparative measurement data for these stable isotopes is different, then it can be determined that the nicotine is not from tobacco; and if the comparative measurement data is similar, then it can be determined that the nicotine is from tobacco. For example, natural nicotine has a $\delta^{13}C$ ($^{13}C/^{12}C$) around −30 to −32 parts per mil relative to the international standard PDB (±σ). In contrast, according to embodiments of the present invention, the synthetic nicotine may have a $\delta^{13}C$ of about −20 to about −29 parts per mil relative to the international standard PDB (±σ), or about −23 to about −29 parts per mil relative to the international standard PDB (±σ). In some embodiments, for example, the synthetic nicotine may have a $\delta^{13}C$ of about −25 to about −28.5 parts per mil relative to the international standard PDB (±σ), or about −26 to about −28.5 parts per mil relative to the international standard PDB (±σ). As such, the synthetic nicotine according to embodiments of the present invention may have a $\delta^{13}C$ that is about 66% to about 97% that of natural nicotine, or about 76% to about 97% that of nicotine. For example, in some embodiments, the synthetic nicotine according to embodiments of the present invention may have a $\delta^{13}C$ that is about 83% to about 95% that of natural nicotine, or about 87% to about 95% that of nicotine.

Additionally, natural nicotine has a δD (D/H) around −170 to −171 parts per mil relative to the international standard V-SMOW (±σ). In contrast, according to embodiments of the present invention, the synthetic nicotine may have a SD of about −140 to about −160 parts per mil relative to the international standard V-SMOW (±σ), or about −145 to about −160 parts per mil relative to the international V-SMOW (±σ). In some embodiments, for example, the synthetic nicotine may have a δD of about −150 to about −160 parts per mil relative to the international standard V-SMOW (±σ), or about −152 to about −158 parts per mil relative to the international standard V-SMOW (±σ). As such, the synthetic nicotine according to embodiments of the present invention may have a δD that is about 82% to about 95% that of natural nicotine, or about 85% to about 95% that of nicotine. For example, in some embodiments, the synthetic nicotine according to embodiments of the present invention may have a δD that is about 88% to about 95% that of natural nicotine, or about 89% to about 93% that of natural nicotine.

As discussed above, the nicotine replacement compositions or NRT compositions according to embodiments of the present invention include a nicotine product. The nicotine replacement composition may be a solid or liquid mixture and may be incorporated into a nicotine replacement product, such as, for example, a smoking cessation patch or gum. In some embodiments, for example, the nicotine replacement composition may comprise about 0.001 wt % to about 25 wt %, for example about 0.01 wt % to about 10 wt %, or about 0.1 wt % to about 1 wt % of the nicotine product based on the total weight of the nicotine replacement composition.

However, the total amount of the nicotine product in a nicotine replacement composition will vary depending on the application, e.g., depending on the type of nicotine replacement product for which the nicotine replacement composition is intended. For example, a smoking cessation patch may incorporate a nicotine replacement composition having a different concentration of the nicotine product than the nicotine replacement composition of a smoking cessation gum. Additionally, a nicotine replacement product may have nicotine replacement compositions having varying concentrations of the nicotine product, for example, a set of products having progressively lesser amounts of the nicotine product in order to gradually wean a user off of nicotine as a means for treating or addressing that user's nicotine addiction. In some embodiments, for example, a user may begin using a first nicotine replacement product (e.g., a gum or patch) incorporating a first nicotine replacement composition having a first concentration of the nicotine product, and then move to using a second nicotine replacement product (e.g., a gum or patch) incorporating a second nicotine replacement composition having a second concentration of the nicotine product that is lower than the first concentration of nicotine. Any number of additional nicotine replacement compositions having lower or higher concentrations of the nicotine product could also be used in such a regimen. Accordingly, it is understood that the nicotine concentrations described here are simply examples of suitable concentrations, and that embodiments of the present invention are not limited to these values. With that in mind, in some embodiments, a nicotine replacement product may include a nicotine replacement composition providing a dosage of nicotine of about 0.1 to about 10 mg/dose, for example, about 0.5 to about 8 mg/dose, or about 1.5 to about 6 mg/dose. In some embodiments, for example, a nicotine replacement product may include a nicotine replacement composition providing a dosage of nicotine of about 3 to about 6 mg/dose.

At least a portion of the nicotine product present in the nicotine replacement composition is synthetic. As used herein, the term "synthetic" means that the identified compound (e.g., nicotine) is prepared through a chemical process that does not include deriving/extracting the nicotine from a naturally occurring source, such as tobacco leaves. The terms "tobacco derived," "natural" and "non-synthetic" are used interchangeably herein, and refer to the identified compound or composition that is derived from or extracted from a natural source (such as, for example, tobacco). For example, as used herein, "tobacco derived nicotine," "natural nicotine" and "non-synthetic nicotine" refer to nicotine derived from or extracted from tobacco leaves, and does not encompass nicotine produced from independent chemical synthesis. In aspects of embodiments of the present invention, the relative portion of the nicotine product that is synthetic is not particularly limited, and may be any suitable amount. For example, as a portion of the total amount of the nicotine product present in the nicotine replacement composition, the synthetic nicotine may be present in an amount of about 0.1 wt % or greater, for example about 0.5 wt % or greater, about 1.0 wt % or greater, about 20 wt % or greater, about 30 wt % or greater, about 40 wt % or greater, about 50 wt % or greater, about 60 wt % or greater, about 70 wt % or greater, about 80 wt % or greater, about 90 wt % or greater, about 95 wt % or greater, about 98% or greater, about 99% or greater, about 99.5% or greater, or in a positive amount (i.e., greater than 0%) up to about 100 wt %. When less than 100 wt % of the nicotine product in the nicotine replacement composition is synthetic, the remaining portion of the nicotine product may be tobacco-derived nicotine.

According to some embodiments, the synthetic nicotine in the nicotine replacement composition may be prepared by any suitable process, nonlimiting examples of which include the processes disclosed in U.S. Pat. Nos. 8,367,837, 8,378,110 and 8,389,733 and European Patent No. EP 2487172, the entire contents of all of which are incorporated herein by reference. For example, in some embodiments, as described generally in U.S. Pat. Nos. 8,367,837, 8,378,110 and 8,389,733 and European Patent No. EP 2487172 to Divi, et al., 1-(but-1-enyl)pyrrolidin-2-one may be condensed with nicotinic acid ester to give 1 (but-1-enyl)-3-nicotinoylpyrrolidin-2-one, which may then be treated with an acid and base to give myosamine, which, in turn, is converted to (R,S)-nicotine by reduction and subsequent N-methylation. An example of this reaction scheme is shown below, reproduced from U.S. Pat. Nos. 8,367,837, 8,378,110 and 8,389,733 and European Patent No. EP 2487172 to Divi, et al.

In some embodiments, the synthetic nicotine in the nicotine replacement composition may be prepared by the synthetic route outlined in Scheme 1:

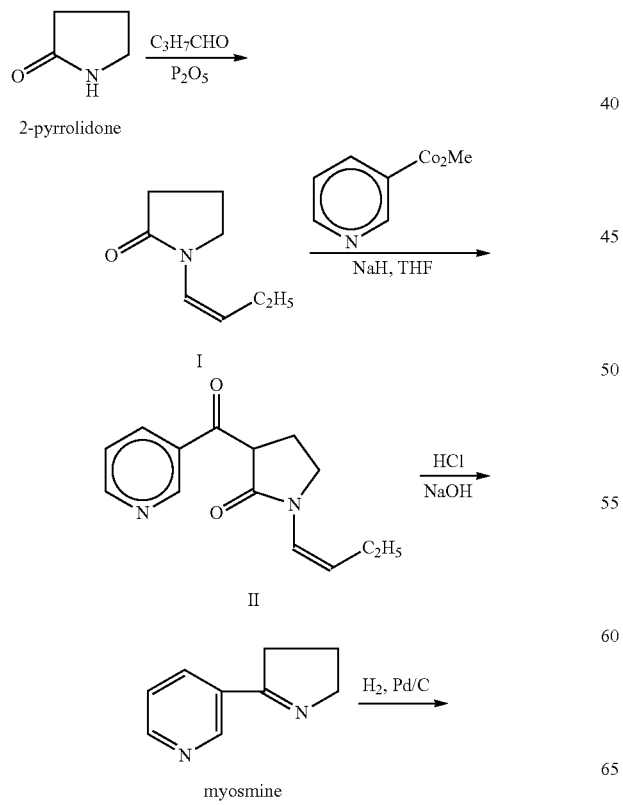

In the synthetic route depicted in Scheme 1, a carbon-carbon bond forming condensation is first performed under anhydrous conditions. In this condensation, an appropriate nicotinate ester (1) is condensed with a suitable N-vinylogous-2-pyrrolidinone (2) under mild conditions, utilizing a suitable dry solvent in combination with a suitable strong base, for example a metal hydride. This condensation gives good yield of the condensation adduct (as its metal salt).

In some embodiments, the condensation reaction mixture utilizes alkyl esters of nicotinic acid in combination with N-vinyl-2-pyrrolidinone, and a metal hydride base in a suitable dry solvent. In some embodiments, the nicotinate alkyl ester comprises short chain alkyl groups (for example, R1 in compound (1) may be $C_{1-3}$, or in some embodiments $C_2$). In some embodiments, the N-vinylogous-2-pyrrolidinone may comprise a vinyl substituent with a short chain alkyl group. In some embodiments, R2 in compound (2) may be a short chain (e.g., $C_{1-10}$) alkyl (such as, e.g., methyl, isopropyl, etc.), or in some embodiments, $R_2$ is hydrogen (H). In some embodiments, the N-vinylogous-2-pyrrolidinone is n-vinyl-2-pyrrolidinone.

The amount (in relative moles) of metal hydride utilized in the condensation reaction mixture with respect to 1 part nicotinate ester is about 0.1 part to about 2.5 parts, for example about 1.2 parts to about 2.1 parts, or about 1.8 parts to about 2 parts. In some embodiments, the mole ratio of metal hydride to nicotinate ester is about 1 to 4, for example about 1:2 to about 1.6:2, or about 2:2. In some embodiments, the metal in the metal hydride may be lithium, potassium or sodium, for example potassium or sodium, or in some embodiments, sodium.

The amount of N-vinylogous-2-pyrolidinone with respect to the amount (in mole equivalents) of nicotinate ester utilized in the condensation reaction mixture may be about 0.1 parts to about 10 parts, for example about 0.5 parts to about 3 parts, or about 1.0 part to about 1.2 parts.

The amount of solvent utilized in the condensation reaction mixture with respect to 1 part (in mole equivalents) nicotinate ester may be about 1 parts to about 15 parts, for example about 3 parts to about 10 parts, about 4 parts to about 8 parts, or about 5 parts to about 7 parts. In some embodiments, the solvent may be anhydrous. Nonlimiting examples of suitable solvents include aromatic hydrocarbon or hydrocarbon solvents, dipolar aprotic solvents (such as, for example, dimethylformamide (DMF)), ethers (such as, for example, ethyl ether, tetrahydrofuran (THF) or tetrahydrofuran derivatives), polyethers (such as, for example, "glyme" or "diglyme"), and combinations thereof. Nonlimiting examples of suitable aromatic hydrocarbons or hydrocarbon solvents include alcohols, toluene, xylenes, benzene, and the like. In some embodiments, for example, the solvent is an alcohol, or an alcohol and ether combination. In some embodiments, the solvent may be THF, or a mixture of DMF and ether, and/or a mixture of DMF and a hydrocarbon or aromatic hydrocarbon. In some embodiments, the solvent may be toluene (or benzene). Alcohols such as ethanol, methanol, and/or propanol may be added to help catalyze the condensation, or the alcohol(s) may be used as the only solvent. If an alcohol is to be used as a solvent or co-solvent in the condensation, then the metals sodium, potassium or lithium may be employed in less than or equal to stoichiometric amounts with respect to the nicotinate ester. In some embodiments, the time of solvent addition is such that a mild effervescence is maintained, and an internal temperature of between 50° C. and 80° C. is maintained throughout the addition process. The time of addition varies with volume, but may take place within a matter of minutes to hours.

After addition of the solvent to the nicotinate ester and N-vinylogous-pyrrolidinone, the condensation reaction mixture becomes greenish. This greenish condensation reaction mixture may be stirred, in some embodiments, under an inert atmosphere for an appropriate amount of time in order to complete the reaction. In some embodiments, the greenish condensation reaction mixture may be heated to an internal temperature of about 40° C. to about 110° C., for example about 60° C. to about 100° C., or about 80° C. to about 95° C.

After reacting the nicotinate ester with the N-vinylogous-2-pyrrolidinone, the condensation reaction mixture may contain a reaction product mixture that includes some unreacted starting material (i.e., nicotinate ester, n-vinylogous-2-pyrrolidinone, sodium hydride) as well as the desired reaction products, i.e., the main condensation product which is the nicotinate-n-vinylogous-2-pyrrolidinone adduct (the condensation adduct, an organic bicyclic compound as the metal salt, e.g., 1-(1-alkenyl)-3-nicotinoylpyrrolidine-2-one, where the alkenyl may be ethenyl in some embodiments), the alcohol as the metal salt, and some alcohol that is displaced from the nicotinate ester as the alcohol.

After completion of the reaction that takes place as a result of the action of the condensation reaction mixture, the reaction product mixture may be either injected (or poured) directly into a solution of acid to form an acid reaction mixture. The acid solution may be a boiling acid solution, or a cold acid aqueous solution. In some embodiments, the acid is an aqueous hydrochloric acid solution. In some embodiments, the normality of the acid solution may be about 3 to about 12, for example about 4 to about 7, or about 5 to about 6.

According to some embodiments, the acid reaction mixture may be prepared by cooling the completed condensation reaction mixture to ambient temperature and then injecting the cooled condensation reaction mixture into a cold solution of acid. The amount of the acid may be about 0.25 parts to about 5 parts, for example about 0.5 parts to about 2 parts, or about 0.75 parts to about 1.5 parts with respect to one part of the condensation reaction mixture.

The reaction of the acid reaction mixture yields a biphasic mixture in which the protonated bicyclic pyridine-pyrrolidinone adduct (i.e., protonated condensation adduct) which is soluble in water and insoluble in the organic solvent is present in the aqueous phase (or layer), and any unreacted pyrrolidinone starting material is in the organic phase (or layer). When the reaction is allowed to settle without agitation, two distinct layers are formed, aqueous and organic (non-aqueous), and the product of the reaction is in the aqueous layer, which aqueous layer is then separated and subjected to further reaction or processing.

After the acid addition, the aqueous and organic (non-aqueous) layers are separated, a concentrated acid is added to the separated aqueous layer to form an aqueous reaction mixture. The aqueous reaction mixture is then heated to reflux for an appropriate period of time to complete the reaction.

The amount of concentrated acid added to separated aqueous layer to form the aqueous reaction mixture may be about 0.15 parts to about 1.5 part, for example about 0.2 part to about 0.5 part, or about 0.25 part to about 0.5 part with respect to 1 part of the separated aqueous layer. In some embodiments, the concentrated acid may be 12N hydrochloric acid (concentrated hydrochloric acid [ca37%]).

After reaction of the aqueous reaction mixture is complete, the aqueous reaction mixture is comprised of water, acid, and product (i.e., the protonated acyclic amine salt, e.g., protonated 3-(4-aminobutanyl-1-one)-pyridine).

After reaction of the aqueous reaction mixture is complete, the aqueous reaction mixture may be cooled to −10° C. to 5° C. Then the acidic aqueous reaction mixture (or solution) may be made strongly basic (e.g., having a pH greater than 9) while keeping the temperature at an appropriate level to maintain the reaction. The result of this reaction is the myosamine reaction mixture, which is comprised of myosamine, base, water, and any remaining unreacted materials from the aqueous reaction mixture, as well as any contaminants natural to the reaction. The resulting basic aqueous reaction mixture is extracted with organic solvent, and then the solvent is distilled off to yield crude myosamine. In some embodiments, the organic solvent may be dichloromethane. In some embodiments, the amount of organic solvent may be about 1 part to about 10 parts with respect to the amount of the basic aqueous reaction mixture, for example about 1.5 parts to about 5 parts, or about 2 parts to about 4 parts with respect to the basic aqueous reaction mixture.

In some embodiments, the completed condensation reaction may be injected directly into a hot solution of hydrochloric acid (instead of the cold acid solution described above), resulting in a heterogeneous acid reaction mixture. The heterogeneous acid reaction mixture may be heated using an external bath to enable vigorous reflux, and the vigorous reflux may be continued until the reaction is complete. In embodiments of this hot acid alternative, the solvent for the condensation reaction mixture may be toluene or xylene, or a high boiling point solvent such as diglyme.

In order to reduce the crude myosamine product to a crude nornicotine product, a suitable hydrogenation catalyst is added in a suitable amount to the crude myosamine (3) in solution with an appropriate solvent to form a myosamine reaction mixture. To complete the reduction of myosamine to nornicotine, the myosamine reaction mixture is submitted to an atmosphere of hydrogen gas at a pressure greater than or equal to ambient pressure, but not high enough to reduce the carbons in the pyridine ring.

In some embodiments, the solvent for the myosamine reaction mixture may be an alcoholic solvent, for example, ethanol or isopropanol, although other solvents known in the art of hydrogenation can also be employed. The amount of solvent may be about 3 parts to about 98 parts, for example about 4 parts to about 60 parts, or about 5 parts to about 20 parts solvent with respect to 1 part crude myosamine. In some embodiments, the suitable hydrogenation catalyst may include 10% palladium on carbon, but other catalysts common to the art of catalytic hydrogenation may also be employed, either as a co-catalyst, or as the sole catalyst. The pressure of the hydrogen gas can be about ambient pressure to about 100 atmospheres, for example about ambient pressure to about 75 atmospheres, or about 10 to about 50 atmospheres.

In some embodiments, the myosamine reaction mixture may include a borohydride salt as the reducing agent rather than a hydrogenation catalyst, and the myosamine reaction mixture may undergo different reaction conditions suitable to effect reduction of the myosamine to nornicotine using the borohydride salt.

Completion of the reaction of the myosamine reaction mixture yields a crude nornicotine reaction mixture that includes nornicotine (reduction product), catalyst and solvent, as well as any unreacted starting material (crude myosamine) and unwanted reaction contaminants. Crude nornicotine product (4) is extracted from the crude nornicotine reaction mixture using known extraction methods.

Water, formic acid and formaldehyde are added to the crude nornicotine (4) product to form a crude nicotine reaction mixture. The crude nicotine reaction mixture is heated to an appropriate temperature for a duration which allows for completion of the methylation reaction that affords crude nicotine in good yield.

At the completion of the reaction of the crude nicotine reaction mixture, the resulting mixture contains crude RS-Nicotine product, solvent (water), and any unreacted starting material including formaldehyde and formic acid, as well as reaction contaminating by-products.

The product of the crude nicotine reaction mixture, i.e., crude RS-Nicotine, may be subjected to at least one high vacuum distillation to give pure (i.e., greater than 95% pure, for example greater than 97% pure, greater than 99% pure, or greater than 99.5% pure) RS-Nicotine as a clear, colorless non-viscous liquor in good overall yield.

The synthetic nicotine produced according to the above-described chemical synthesis is substantially free or completely free of certain contaminants typically found in the natural nicotine derived from tobacco leaves. In some embodiments, the synthetic nicotine may be substantially free of these contaminants, such that the combined amount of these contaminants in the synthetic nicotine may be more than 0 wt % but less than 0.5 wt %, for example less than 0.2 wt %, less than 0.01 wt %, less than 0.001 wt %, less than 0.0001 wt %, or less than 0.00001 wt % based on the total weight of the synthetic nicotine. As discussed above, "completely free" or "free" of these contaminants means that the synthetic nicotine includes no measurable amount of these contaminants, i.e., 0 wt % (or none). In some embodiments, the synthetic nicotine is substantially free or completely free of contaminants such as alkaloid compounds, which may be found in nicotine derived from tobacco. For example, the synthetic nicotine may be substantially free or completely free of one or more or all of nicotine-1'-N-oxide, nicotyrine, nornicotyrine, 2',3-bipyridyl, anabasine, and anatabine. While these contaminants may be among the most common impurities or contaminants in tobacco-derived nicotine, other naturally occurring contaminants or impurities may be present in tobacco-derived nicotine, and the synthetic nicotine according to embodiments of the present invention is substantially free or completely free of those contaminants and impurities as well.

However, while the synthetic nicotine according to embodiments of the present invention may be substantially free or completely free of certain contaminants normally found in tobacco-derived nicotine, as discussed above, the synthetic nicotine may include certain other impurities or contaminants resulting from the synthetic route. Although such contaminants and impurities may be present in the synthetic nicotine according to embodiments of the present invention, these impurities are not generally present in tobacco-derived or naturally sourced nicotine. Indeed, the contaminants/impurities found in naturally sourced (or tobacco-derived) nicotine are significantly different than those potentially found in the synthetic nicotine according to embodiments of the present invention. For example, the contaminants or impurities present in the synthetic nicotine according to embodiments of the present invention may include one or more or all of myosamine, nornicotine, water, and the solvents (discussed above) used in the various reactions of the synthesis scheme. Additionally, in some embodiments, the contaminants or impurities present in the synthetic nicotine may include one or more or all of 1-keto-5-methylamino, or 1-hydroxy-5-methylamino-2-pyridine. As used herein, the terms "synthetic contaminants," "synthetic impurities," and like terms, are used interchangeably, and refer to these contaminants and/or impurities found in the synthetic nicotine according to embodiments of the present invention but not typically found in naturally sourced (or tobacco-derived) nicotine.

For example, based on the total weight of the synthetic nicotine, the synthetic nicotine may include about 0 wt % (i.e., an undetectable, or unmeasurable amount) to about 5 wt %, for example about 0 wt % (i.e., an undetectable, or unmeasurable amount) to about 1 wt %, about 0 wt % (i.e., an undetectable, or unmeasurable amount) to about 0.5 wt % myosamine. In some embodiments, based on the total weight of the synthetic nicotine, the synthetic nicotine may include about 0 wt % (i.e., an undetectable, or unmeasurable amount) to about 5 wt %, for example about 0 wt % (i.e., an undetectable, or unmeasurable amount) to about 3 wt %, or about 0 wt % (i.e., an undetectable, or unmeasurable amount) to about 1 wt % nornicotine. In some embodiments, based on the total weight of the synthetic nicotine, the synthetic nicotine may include about 0 wt % (i.e., an undetectable, or unmeasurable amount) to about 5 wt %, for example about 0 wt % (i.e., an undetectable, or unmeasurable amount) to about 3 wt %, or about 0 wt % (i.e., an undetectable, or unmeasurable amount) to about 1 wt % solvent. Also, in some embodiments, based on the total weight of the synthetic nicotine, the synthetic nicotine may include about 0 wt % (i.e., an undetectable, or unmeasurable amount) to about 5 wt %, for example about 0 wt % (i.e., an undetectable, or unmeasurable amount) to about 3 wt %, or about 0 wt % (i.e., an undetectable, or unmeasurable amount) to about 1 wt % water.

The above-described synthesis of nicotine produces a racemic mixture, i.e., a 50-50 mixture of the R and S isomers of nicotine. Thus, in some embodiments, the synthetic nicotine includes a ratio of the R-isomer to the S-isomer of 1:1. However, in some embodiments, the ratio of the R-isomer to the S-isomer can be manipulated through further resolution of the synthetic nicotine. For example, the synthetic nicotine may have a ratio of the R-isomer to the S-isomer of about 1:1 to about 1:1000, about 1:1.1 to about 1:100, about 1:2 to about 1:5, about 1:4 to about 1:9, or about 1:5 to about 1:7. In some embodiments, the synthetic nicotine may include a ratio of the R-isomer to the S-isomer of about 1:1 to about 1000:1, about 1.1:1 to about 100:1, about 2:1 to about 5:1, about 4:1 to about 9:1, or about 5:1 to about 7:1.

In some exemplary embodiments, for example, the synthetic nicotine includes a ratio of the S-isomer to the R-isomer of less than 50:1, for example 45:1 or lower, 40:1 or lower, or 35:1 or lower. In some embodiments, the synthetic nicotine may include a ratio of the R-isomer to the S-isomer of less than 50:1, for example 45:1 or lower, 40:1 or lower, or 35:1 or lower. Additionally, in some embodiments, the synthetic nicotine may include the R-isomer in an amount greater than 5 wt %, for example, greater than 7 wt %, or greater than 10 wt %. In some embodiments, the synthetic nicotine may include the S-isomer in an amount greater than 5 wt %, for example, greater than 7 wt %, or greater than 10 wt %. In some embodiments, the synthetic nicotine includes more R-isomer than S-isomer, and in some embodiments, the synthetic nicotine includes more S-isomer than R-isomer.

This ratio of R/S isomers in the synthetic product is yet another characteristic that distinguishes the synthetic nicotine according to embodiments of the present invention from natural or tobacco-derived nicotine. Indeed, a simple test to determine chirality of the sample can be performed in order to determine whether the sample includes natural nicotine or a synthetic nicotine according to embodiments of the invention. Techniques for determining chirality or optical rotation of a sample are known to those of ordinary skill in the art, and the ordinary artisan would be readily capable of selecting an appropriate technique and carrying out that technique to determine chirality or optical rotation. One nonlimiting example of such a technique is high performance liquid chromatography (HPLC) using a chiral column. For example, the optical rotation of the sample may first be determined by any suitable technique (which are known to those of ordinary skill in the art), and then the sample may be run through the chiral column and the results compared to the USP standard for tobacco-derived or natural nicotine.

The synthetic nicotine containing the racemic mixture of R and S isomers may be resolved to have these relative amounts of the R and S isomers by any suitable resolution techniques, which techniques are known to those skilled in the art (e.g., crystallization, chromatography, etc.). Additionally, in some embodiments, the synthesized nicotine may be fully resolved to yield either pure R-isomer or pure S-isomer. As used herein, the term "pure" as used in defining the isomeric composition of the synthetic nicotine, refers to a percentage of the identified isomer of greater than 97%, for example greater than 98%, and in some embodiments greater than 99%. For example, a "pure S isomer" synthetic nicotine includes a synthetic nicotine that has been resolved to include a ratio of S isomer to R isomer of greater than 97:3, for example greater than 98:2, and in some embodiments, greater than 99:1. Similarly, a "pure R isomer" synthetic nicotine includes a synthetic nicotine that has been resolved to include a ratio of R isomer to S isomer of greater than 97:3, for example greater than 98:2, and in some embodiments, greater than 99:1. In some embodiments, however, a pure R isomer may include 100% R isomer with 0% S isomer, and a pure S isomer may include 100% S isomer with 0% R isomer.

As noted above, any suitable resolution technique may be used to resolve the synthetic nicotine composition, which techniques are known to those of ordinary skill in the art. Some nonlimiting examples of resolution techniques include those described in Divi et al., U.S. Patent Publication No. 2012/0197022, filed Apr. 6, 2011, Aceto, et al., *J. Med. Chem.*, "Optically Pure (+)-Nicotine from (±)-Nicotine and Biological Comparisons with (−)-Nicotine vol. 22, pgs. 174-177 (1979), and DeTraglia et al., "Separation of D-(+)-Nicotine from a Racemic Mixture by Stereospecific Degradation of the L-(−) Isomer with *Pseudomonas putida*," *Applied and Environmental Microbiology*, vol. 39, pgs. 1067-1069 (1980), the entire contents of all of which are incorporated herein by reference. For example, as described in Aceto et al., resolution of the racemic mixture may be accomplished using D-tartaric acid, and as described in DeTraglia et al., resolution can be accomplished using *Pseudomonas putida*. In addition, in some embodiments, resolution of the racemic mixture may be accomplished using (+)-O,O'-di-p-toluoyl-D-tartaric acid. Additionally, as described in Divi et al., resolution of the racemic mixture may be accomplished by diastereomeric salt formation using dibenzoyl-D-tartaric acid and dibenzoyl-L-tartaric acid to achieve separation.

In some embodiments, however, the racemic mixture may be blended or mixed with suitable added amounts of pure R isomer or pure S isomer, which pure isomers would typically be prepared via enantioselective synthetic pathways. Notably, naturally sourced nicotine (i.e., that derived from tobacco leaves) generally has an undetectable or small amount of the R isomer, and typically the naturally sourced tobacco mainly includes the S isomer. Indeed, naturally sourced tobacco typically has an S to R isomer ratio of greater than 50:1.

As discussed above, according to some embodiments of the present invention, the synthetic nicotine may include a mixture of the R and S isomers, whether racemic or otherwise. As would be understood by those of ordinary skill in the art, tobacco-derived (or naturally sourced) nicotine typically has greater than 95 wt % of the S isomer, and therefore is optically active. Indeed, when measured using a standard polarimeter, the tobacco-derived nicotine (having 95 wt % or greater S nicotine isomer) registers a negative optical rotation which is typically greater than 125°. In contrast, according to embodiments of the present invention, the synthetic nicotine may include a racemic (or 1:1) mixture of the R and S isomers, yielding a nicotine having no optical rotation. Additionally, in embodiments of the present invention in which the synthetic nicotine includes a non-racemic mixture of the R and S isomers, the synthetic product will register an optical rotation that is different from the optical rotation of tobacco-derived nicotine (i.e., due to the presence of the R isomer, which generally has an opposite optical rotation than that of the S isomer).

As discussed above, tobacco-derived (or naturally sourced) nicotine may include one or more or all of the following impurities: nicotine-1'-N-oxide, nicotyrine, nornicotyrine, 2',3-bipyridyl, cotinine, anabasine, anatabine, nornicotine, and myosamine. For example, tobacco derived nicotine may comprise 99.5 wt % nicotine, 0.1 wt % nornicotine, 0.15 wt % myosamine, and 0.1 wt % cotinine. According to some embodiments of the present invention, as described above, the nicotine replacement composition or NRT composition may include both the synthetic nicotine described above and an amount of naturally sourced (or tobacco-derived) nicotine. In these embodiments of the nicotine replacement composition including the naturally sourced nicotine, the portion of the composition making up the tobacco-derived nicotine may include these components (or contaminants) in, e.g., the above amounts. However, as would be appreciated by those of ordinary skill in the art, because the naturally sourced nicotine (or tobacco-derived nicotine) makes up only a portion of the nicotine replacement composition or NRT composition, the amount of these natural tobacco contaminants in the overall nicotine replacement composition is significantly lower than the amounts reported above, and significantly lower than the amounts in comparable compositions using larger portions of (or all) naturally sourced nicotine.

In embodiments including a mixture of synthetic nicotine and naturally-sourced or tobacco derived nicotine, the nicotine product of the nicotine replacement composition may include more synthetic nicotine than tobacco-derived nicotine. For example, in such a mixture, based on the total weight of the nicotine product, the nicotine product may include 50 wt % or more synthetic nicotine, for example 60 wt % or more synthetic nicotine or 70 wt % or more synthetic nicotine. In some embodiments, for example, in embodiments including a mixture of synthetic nicotine and tobacco-derived nicotine, based on the total weight of the nicotine product, the nicotine product of the nicotine replacement composition may include 80 wt % or more synthetic nicotine, for example 90 wt % or more synthetic nicotine, or 95 wt % or more synthetic nicotine.

In addition to the nicotine product (i.e., the synthetic nicotine and/or naturally sourced nicotine) discussed above, the composition for use in nicotine replacement products or therapies (i.e., the nicotine replacement composition or NRT composition) may further comprise, consist essentially of, or consist of one or more pharmaceutically acceptable excipients, additives and/or carriers (e.g., solvents). Nonlimiting examples of such excipients, additives and/or carriers (e.g., solvents) include water, organic solvents, resins or polymers (e.g., edible or biocompatible resins or polymers), elastomers, gum bases, and the like, sweetening and/or flavoring agents, pH adjusting agents and the like. Nonlimiting examples of carriers or solvents that may be used in liquid nicotine replacement compositions (such as, for example, those intended for inhalation through a vaping device, or those housed in a reservoir in certain transdermal nicotine delivery patches) include water, and alcohols such as 1,2-propylene glycol (PG or MPG), ethanol, ethyl acetate, 1-3 propanediol, glycerin (e.g., vegetable glycerin) and the like. The solvent may include a single solvent or may include a combination of two or more solvents. The amount of solvent present may be selected based on the NRT product in which the composition is used. In some embodiments, for example in embodiments in which the composition remains liquid, the amount of solvent present may be about 50 wt % to about 99.99 wt %, for example about 75 wt % to about 99 wt %, or about 85 wt % to about 98 wt % based on the total weight of the composition.

In some embodiments, for example, in embodiments in which the nicotine replacement composition is a liquid (e.g., a liquid composition that can be inhaled through a vaping device, or a liquid composition that is housed in a reservoir of a nicotine patch), the nicotine replacement composition may include water as a solvent. The amount of water present in the nicotine replacement composition may vary depending on the NRT product in which the composition is used. In some embodiments, for example, in embodiments in which the nicotine replacement composition is a liquid composition that can be inhaled through a vaping device, the water may be present in an amount of about 0.1 to about 10 wt %, for example about 0.5 to about 5 wt %, based on the total weight of the nicotine replacement composition.

In some embodiments, the nicotine replacement composition may include glycerin as a solvent, and the glycerin may be a Kosher vegetable glycerin having a purity greater than 99%, for example greater than 99.5%, or greater than 99.9%. The glycerin may be odorless, colorless and have a slightly sweet taste.

In some embodiments, the nicotine replacement composition may include propylene glycol as a solvent, and the propylene glycol may be USP grade and have a purity greater than 99%, for example greater than 99.5%, or greater than 99.99%. The propylene glycol may be odorless and colorless, and essentially tasteless. In some embodiments, the nicotine replacement composition may include a solvent that comprises, consists essentially of, or consists of glycerin and propylene glycol.

In some embodiments, for example, in embodiments in which the nicotine replacement composition is intended for use in a resinous or polymeric transdermal nicotine delivery patch, the nicotine replacement composition may include a resin or polymer as a carrier. Any suitable resin or polymer may be used so long as it is compatible with the nicotine replacement composition intended to be housed, embedded or impregnated in the carrier. As the nicotine patch is intended to be in contact with a user's skin, the resin or polymer should also be biocompatible and non-irritating (or only moderately irritating) to the skin. Nonlimiting examples of suitable such polymers and/or resins include polyurethane polymers, methacrylate polymers, ethylene acrylic acid polymers, and the like. Some nonlimiting examples of suitable methacrylate polymers include polymethyl methacrylate and polybutyl methacrylate, and nonlimiting examples of suitable polyurethanes include polyether and polyester polyurethanes. As would be understood by those of ordinary skill in the art, the amount of the polymer or resin will depend on the desired loading level of the nicotine replacement composition, and the skilled artisan would be readily capable of selecting an appropriate amount of polymer to contain, embed or otherwise house the desired amount of the nicotine replacement composition in the polymer matrix.

In some embodiments, for example, in embodiments in which the nicotine replacement composition is intended for use in a nicotine gum, the nicotine replacement composition may include a gum base or similar polymer, or an elastomer as a carrier or solvent. Any suitable gum base or polymer may be used so long as it is compatible with the nicotine replacement composition intended to be housed, embedded or impregnated in the carrier. As the nicotine gum is intended to be chewed by the user, the gum base or polymer should also be edible and biocompatible. Any suitable gum base that is insoluble in water and/or saliva may be used, and such gum bases are well known to those of ordinary skill in the art. Indeed, those of ordinary skill in the art would be readily capable of selecting an appropriate polymer or gum base for use in a nicotine gum. Nonlimiting examples of suitable such polymers and/or gum bases include natural and synthetic elastomers and rubbers, and mixtures thereof. Some nonlimiting examples of suitable naturally occurring polymers include plant derived polymers such as, for example, chicle, jelutong, gutta percha, crown gum, and mixtures thereof. Some nonlimiting examples of suitable synthetic elastomers include butadiene-styrene copolymers, isobutylene and isoprene copolymers (e.g., butyl rubbers), polyethylene, polyisobutylene, polyvinyl esters such as polyvinylacetate, and mixtures thereof. As would be understood by those of ordinary skill in the art, the amount of the polymer or gum base will depend on the desired loading level of the nicotine replacement composition and the desired rate of release of the nicotine replacement composition (e.g., during chewing), and the skilled artisan would be readily capable of selecting an appropriate amount of polymer or gum base to contain, embed or otherwise house the desired amount of the nicotine replacement composition in the polymer matrix.

Additionally, any suitable elastomer solvent may be used, and such elastomer solvents are known to those of ordinary skill in the art. Nonlimiting examples of suitable such elastomer solvents include rosins and resins, and mixtures thereof. Some nonlimiting examples of suitable elastomer solvents include methyl, glycerol, and pentaerythritol esters of rosins or modified rosins, such as hydrogenated, dimerized or polymerized rosins, and mixtures thereof. For example, the elastomer solvent may include a pentaerythritol ester of a partially hydrogenated wood rosin, a pentaerythritol ester of a wood rosin, a glycerol ester of a wood rosin, a glycerol ester of a partially dimerized rosin, a glycerol ester of a polymerized rosin, a glycerol ester of a tall oil rosin, a glycerol ester of a wood rosin and a partially hydrogenated wood rosin and partially hydrogenated methyl ester of rosin, such as polymers of alpha-pinene or beta-pinene, and terpene resins including polyterpenes and mixtures thereof. As would be understood by those of ordinary skill in the art, the amount of the elastomer solvent will depend on the desired loading level of the nicotine replacement composition and the desired rate of release of the nicotine replacement composition (e.g., during chewing), and the skilled artisan would be readily capable of selecting an appropriate amount of elastomer solvent to contain, embed or otherwise house the desired amount of the nicotine replacement composition in the carrier.

In some embodiments, the pH of the nicotine replacement composition may be adjusted (e.g., to improve the taste or experience of a nicotine gum or vaping liquid, or the feel or irritation of a transdermal nicotine delivery patch) by the addition of pharmacologically or pharmaceutically acceptable acids as pH adjusting agents. In some embodiments, the acid pH adjusting agent may be an inorganic acid. Nonlimiting examples of suitable inorganic acid pH adjusting agents include: hydrochloric acid, hydrobromic acid, nitric acid, sulfuric acid and/or phosphoric acid. In some embodiments, the inorganic acid may include hydrochloric acid and/or sulfuric acid (i.e., an inorganic acid or a mixture of inorganic acids).

In some embodiments, the acid pH adjusting agent may be an organic acid. Nonlimiting examples of suitable organic acids include: lactic acid, ascorbic acid, citric acid, malic acid, tartaric acid, maleic acid, succinic acid, fumaric acid, acetic acid, formic acid and/or propionic acid, and the like. In some embodiments, for example, the organic acid may be lactic acid, ascorbic acid, fumaric acid and/or citric acid (i.e., an organic acid or a mixture of organic acids). For example, in some embodiments, the organic acid includes citric acid and/or lactic acid.

In some embodiments, the acid pH adjusting agent may be an acid which forms an acid addition salt with the active substance. Also, if desired, a single acid pH adjusting agent may be used, or a mixture of two or more acid pH adjusting agents may be used. Indeed, some acids have additional properties that make them desirable for inclusion in the vaping composition. For example, some acids may have pH adjusting (or acidifying) properties in addition to auxiliary or additional properties, such as, e.g. flavoring properties or antioxidant properties. Some nonlimiting examples of such dual function acids include citric acid and ascorbic acid.

In some embodiments, the pH adjusting agent may be basic, or the nicotine replacement composition may include an additional pH adjusting agent that is basic (e.g., in addition to the acidic pH adjusting agent). For example, a basic pH adjusting agent may be used or desired to more precisely titrate the pH of the nicotine replacement composition. Accordingly, in some embodiments, the pH adjusting agent may include (or further include) a basic pH adjusting agent, which may include a pharmacologically acceptable base. Nonlimiting examples of suitable such bases include alkali metal hydroxides and alkali metal carbonates. In some embodiments, the alkali ion in the alkali metal hydroxides or carbonates may be sodium. In embodiments in which such a basic pH adjusting agent is used, as would be understood by those of ordinary skill in the art, care must be taken to ensure that the resulting salts, which are then contained in the finished pharmaceutical formulation, are pharmacologically compatible with the abovementioned acid of the acid pH adjusting agent.

As would be understood by those skilled in the art, the amount of the pH adjusting agent (whether acid or base) will depend on the desired target pH and the starting pH of the composition. Indeed, pH adjustment and titration techniques and addition amounts are well within the knowledge and skill of the ordinary artisan in this field.

In some embodiments, as discussed above, the nicotine replacement composition may further include a pharmacologically or pharmaceutically acceptable excipient. The excipient may include any of a number of compounds, some nonlimiting examples of which include antioxidants, such as ascorbic acid (which can also be used to adjust the pH as discussed above), vitamin A, vitamin E, tocopherols and similar vitamins or provitamins occurring in the human body.

Other nonlimiting examples of suitable excipients include preservatives, which can be added to protect the formulation from contamination by, for example, pathogenic bacteria. Any suitable preservative may be used, including those known in the art. Some nonlimiting examples of suitable preservatives include butylated hydroxyl toluene, benzalkonium chloride, benzoic acid or benzoates such as sodium benzoate. In some embodiments, the preservative may include benzalkonium chloride. Any suitable amount of the preservative may also be used, which amount (or concentration) would be known to those skilled in the art.

Additional nonlimiting examples of suitable excipients include plasticizers and softeners, which can be added to adjust the viscosity of the nicotine replacement composition. In some embodiments, for example, in embodiments in which the nicotine replacement composition is intended for use in a nicotine gum, the nicotine replacement composition may include a plasticizer and/or softener in order to improve the texture and bite of the gum during chewing. Any suitable plasticizers and/or softeners can be used, including those known in the art. However, in embodiments in which the nicotine replacement composition is intended for use in an edible product (such as, for example, in a nicotine gum), the plasticizers and/or softeners should be fit for human consumption, non-toxic and biocompatible. Some nonlimiting examples of suitable plasticizers and/or softeners include lecithin, mono- and di-glycerides, lanolin, stearic acid, sodium stearate, potassium stearate, glycerol triacetate, glycerol monostearate, glycerin, waxes (such as, for example beeswax), fats and oils (such as, for example, soybean and/or cottonseed oils). Any suitable amount of the plasticizer and/or softener may be used, which amount (or concentration) would be known to those of ordinary skill in the art. Also, the desired viscosity or softness of the composition may vary depending on the intended application of the nicotine replacement composition, and those of ordinary skill in the art would be readily capable of selecting an appropriate plasticizer and/or softener and an appropriate amount of these excipients in order to achieve the desired properties.

As discussed above, fats and oils can be included in the nicotine replacement composition as a plasticizer and/or softener. However, the fats and oils may also be included in the nicotine replacement composition as an encapsulating agent that encapsulates or surrounds the active ingredient, i.e., the nicotine product. This encapsulation can aid in creating a uniform product, and provide added shelf-life by improving the stability of the nicotine replacement composition. Nonlimiting examples of suitable such fats and oils for encapsulation include vegetable and animal fats and oils, such as, for example, stearine, mono-e and di-glyceride-based fats. In some embodiments, for example, the encapsulating agent may include stearine, canola oil, cottonseed oil, soybean oil, medium chain triglycerides oils, mono-, di- and tri-glyceride-based fatty acid oils. Any suitable amount of the encapsulating agent may be used, which amount (or concentration) would be known to those of ordinary skill in the art. Also, the desired properties of the composition may vary depending on the intended application of the nicotine replacement composition, and those of ordinary skill in the art would be readily capable of selecting an appropriate encapsulating agent and an appropriate amount of these excipients in order to achieve the desired properties.

Other nonlimiting examples of suitable excipients include fillers, which can be added to adjust the properties of the nicotine replacement composition. In some embodiments, for example, in embodiments in which the nicotine replacement composition is intended for use in a nicotine gum, the nicotine replacement composition may include a filler in order to improve the texture and bite of the gum and the chewability. The filler may also be added to adjust the release of nicotine from the composition, and the absorption of nicotine by the user. Any suitable fillers can be used, including those known in the art. However, in embodiments in which the nicotine replacement composition is intended for use in an edible product (such as, for example, in a nicotine gum), the fillers should be fit for human consumption, non-toxic and biocompatible. Some nonlimiting examples of suitable fillers include calcium carbonate, magnesium silicate (i.e., talc), dicalcium phosphate, metallic mineral salts (such as, for example, alumina, aluminum hydroxide, and aluminum silicates), and mixtures thereof. Any suitable amount of the filler may be used, which amount (or concentration) would be known to those of ordinary skill in the art. Also, the desired properties of the composition may vary depending on the intended application of the nicotine replacement composition, and those of ordinary skill in the art would be readily capable of selecting an appropriate filler and an appropriate amount of these excipients in order to achieve the desired properties.

In some embodiments, the nicotine replacement composition may further comprise a sweetening and/or flavoring agent. Any suitable such sweetener and/or flavoring agent may be used, some nonlimiting examples of which include sugars, sugar substitutes, sugar alcohols, peppermint, menthol, wintergreen, spearmint, propolis, eucalyptus, cinnamon, oils or the like. Some additional nonlimiting examples of suitable flavorants or sweeteners include those derived from fruits, tobacco itself, liquor, coffee and confectionaries. The amount of the sweetener and/or flavorant may be about 0 wt % (e.g. no flavorant is present, or no flavorant is added) to about 40 wt %, for example about 1 wt % to about 30 wt %, about 5 wt % to about 20 wt %, or about 10 wt % to about 15 wt %, based on the total weight of the nicotine replacement composition. In some embodiments, the amount of the sweetener and/or flavorant may be about 10 wt % based on the total weight of the nicotine replacement composition.

It has been surprisingly found that the nicotine replacement compositions according to embodiments of the present invention including a portion of synthetic nicotine has suitable and/or enhanced physiological activity on the human system, including neuroactivity, as well as suitable and/or enhanced sensory appeal (e.g., mouthfeel, throatfeel, etc.) as compared to compositions including only nicotine derived from tobacco (or naturally sourced nicotine) as the nicotine component. Indeed, smoker/vaporizer users have found that the compositions according to embodiments of the present invention including at least a portion of synthetic nicotine to be preferable to compositions using only nicotine derived from tobacco (or naturally sourced nicotine) as the nicotine component.

Also, because the nicotine replacement compositions described herein have fewer of the contaminants associated with tobacco-derived nicotine, smaller amounts (if any at all) of sweeteners and/or flavorants are needed in the compositions. In particular, smaller amounts of sweeteners and/or flavorants are needed to mask the bitterness and smell of comparable compositions comprising only tobacco-derived nicotine as the nicotine component. In some embodiments, the nicotine replacement composition is substantially free of sweeteners and/or flavorants.

Using smaller amounts of sweeteners and/or flavorants (or substantially no sweeteners and/or flavorants) provides certain benefits to the nicotine replacement products. For example, smaller amounts of sweeteners and/or flavorants (or substantially no sweeteners and/or flavorants) provides a mechanical benefit to electronic vaping devices. Specifically, the use of smaller amounts of sweeteners and/or flavorants leads to less wear on the coil or heating element of the vaporizer. Because sweeteners and/or flavorants tend to be sticky, oily or more viscous than the other components in the nicotine replacement composition, the addition of larger amounts of sweeteners and/or flavorants causes the coil (or heating element) to work harder to heat the nicotine replacement composition. Also, because of the sticky, oily, viscous properties of the sweeteners and/or flavorants, compositions having larger amounts of sweeteners and/or flavorants tend to have larger amounts of buildup on the coil, which also increases wear on the coil, and decreases the working life of the coil (and device). In contrast, in the nicotine replacement compositions according to embodiments of the present invention, smaller amounts of the sweeteners and/or flavorants are used, reducing the wear on the coil, and the potential for buildup on the coil. As a result, the nicotine replacement compositions according to embodiments of the present invention can increase the working life of the coil or heating element, and thus the life of the vaping device.

Additionally, in embodiments of nicotine replacement products that are edible (such as, for example, a nicotine gum or other confection), smaller amounts of sweeteners reduces the amount of sugars in the product, which makes the product more appealing to many consumers or users. Indeed, increased amounts of sweeteners may lead to several undesirable human health consequences, such as weight gain, compromised immune system, diabetes and other chronic diseases, as well as a variety of dental concerns. Accordingly, the smaller amounts of sweeteners in the nicotine replacement compositions according to embodiments of the present invention yield a healthier option for treating nicotine addiction. Also, the reduced amount of flavorants in the nicotine replacement compositions according to embodiments of the present invention leads to products with a more pleasant taste that is less intensely flavored, which appeals to a large number of users.

In some embodiments, the nicotine replacement composition may be intravenously injected. In such embodiments, the injectable composition may include any of the nicotine replacement compositions described herein in which the carrier is a pharmaceutically acceptable carrier suitable for intravenous delivery, which pharmaceutically acceptable carriers are well known to those of ordinary skill in the art.

In accordance with aspects of embodiments of the present invention, a (1) 50-50 RS synthetic nicotine provides the same or better sensory impact as "S" nicotine derived from tobacco. Similarly, a (2) racemic synthetic nicotine is neurologically effective, and in many cases exhibits superior neurological effect to that of tobacco-derived ("S") nicotine. Also, the above-disclosed blends of synthetic RS nicotine with synthetic or non-synthetic tobacco-derived nicotine, according to embodiments of the present invention, have improved sensory impact as well as neurological impact on the user as compared to nicotine replacement compositions having only tobacco-derived nicotine as the source of nicotine. Additionally, having fewer tobacco alkaloids in the nicotine replacement composition increases the shelf life of the composition and maintains visual clarity of product (e.g., a colorless or transparent appearance).

The nicotine replacement compositions according to embodiments of the present invention, especially those that are completely free of any tobacco-derived nicotine or its associated impurities, have reduced carcinogensis, or are not carcinogenic. Indeed, synthetic nicotine is not carcinogenic, as discussed in Carmella, et al., "Evidence for endogenous formation of tobacco-specific nitrosamines in rats treated with tobacco alkaloids and sodium nitrite," *Carcinogensis*, vol. 18, no. 3, pp 587-592 (1997), the entire content of which is incorporated herein by reference. In contrast, tobacco-derived nicotine is carcinogenic due to the presence of the contaminants discussed herein. Accordingly, in some embodiments, the nicotine replacement compositions (regardless of isomeric composition) are non-carcinogenic.

According to some embodiments of the present invention, a nicotine replacement therapy product (NRT product) utilizes the nicotine replacement compositions described above. Any suitable NRT product may use the nicotine replacement compositions according to embodiments of the present invention, some nonlimiting examples of which include a transdermal nicotine replacement delivery patch (also referred to herein as a "nicotine patch" or "transdermal nicotine delivery patch"), a nicotine replacement gum (also referred to herein as a "nicotine gum"), a nicotine replacement chewing tobacco (e.g., a composition having properties similar to conventional chewing tobacco), a nicotine replacement snuff (e.g., a composition having properties similar to conventional snuff), a nicotine replacement strip (e.g., a composition having properties similar to conventional dissolvable tobacco), a nicotine replacement oral spray, and a lotion, balm, salve or other type of rub incorporating a nicotine replacement composition. Several variations of these nicotine replacement therapy products are well known to those of ordinary skill in the art, and the NRT products according to embodiments of the present invention are the same as the known products except that the nicotine source is replaced with the nicotine replacement compositions described herein. As the structure, function, and manufacturing methods for each of these NRT products is well known to those of ordinary skill in the art, those of ordinary skill in the art would be readily capable of replacing the existing nicotine source with the nicotine replacement compositions according to embodiments of the present invention.

By way of example, a NRT product according to embodiments of the present invention includes a transdermal nicotine replacement delivery patch. The transdermal nicotine replacement delivery patch may have a similar structure and composition to the patches disclosed in U.S. Pat. No. 4,943,435 to Baker et al., and titled "Prolonged Activity Nicotine Patch," the entire content of which is incorporated herein by reference. However, the transdermal nicotine replacement delivery patch uses the nicotine replacement compositions according to embodiments of the present invention in place of the "nicotine" described in the patent document. For example, a transdermal nicotine replacement delivery patch according to embodiments of the present invention may include an impermeable support layer, a nicotine replacement composition layer, and either a release liner or a nicotine replacement composition permeable layer. The impermeable support layer may include any suitable material that is both capable of supporting the nicotine replacement composition layer and that prevents or minimizes the permeation of the nicotine replacement composition through the impermeable support layer. Indeed, while the term "impermeable" is intended to convey that the nicotine replacement composition generally does not permeate through the impermeable support layer it is understood that the impermeable support layer may not be perfectly impermeable, and that some, negligible amounts of the nicotine replacement composition may permeate through the layer over time. Suitable materials for the impermeable support layer are well known to those of ordinary skill in the art, and any of these materials may be used in the transdermal nicotine delivery patch according to embodiments of the present invention. Some nonlimiting examples of suitable impermeable support layer materials include polyesters, aluminized polyesters, metal foils, metallized polyfoils, composite foils or films containing polyester, polytetrafluoroethyelene materials, and the like.

The nicotine replacement composition layer may include any of the nicotine replacement compositions according to embodiments of the present invention, and may be a liquid, or may be embedded in a resinous or polymeric matrix. When the nicotine replacement composition is provided as a liquid, the nicotine replacement composition layer may be a reservoir housing the nicotine replacement composition, and the patch may include the nicotine replacement composition permeable layer. When the nicotine replacement composition is embedded in a resinous or polymeric matrix, the matrix makes up the nicotine replacement composition layer, and the patch includes the release liner releasably attached to the nicotine replacement composition layer (i.e., the matrix). In some embodiments, however, when the nicotine replacement composition layer is a reservoir housing the nicotine replacement composition, the patch may include both the nicotine replacement composition permeable layer (or membrane) and a release liner releasably attached to the nicotine replacement composition permeable layer.

In embodiments in which the nicotine replacement composition layer is a reservoir housing the nicotine replacement composition, the nicotine replacement composition may include any of the nicotine replacement compositions in liquid form described herein. Additionally, the nicotine replacement composition permeable layer may be any suitable material capable of permeating the nicotine replacement composition at the desired permeation rate. Suitable materials for the nicotine replacement composition permeable layer are well known to those of ordinary skill in the art, and any of these materials may be used in the transdermal nicotine delivery patch according to embodiments of the present invention. Indeed, those of ordinary skill in the art would be readily capable of selecting a suitable material for the nicotine replacement composition permeable layer based on the desired composition permeation rate, and compatibility with the components of the nicotine replacement compositions. Some nonlimiting examples of suitable nicotine replacement composition permeable layer materials include various polyethylenes, polyamides and ethylene vinyl acetate copolymers.

Also, release liners are well known in the art, and any suitable release liner material may be used in connection with embodiments of the transdermal nicotine replacement deliver patch. In some embodiments, for example, the release liner may be any suitable silicone release liner.

As another example, a NRT product according to embodiments of the present invention includes a nicotine replacement gum. The nicotine replacement gum may have a similar structure and composition to the gums disclosed in U.S. Pat. No. 6,344,222 to Cherukuri et al., and titled "Medicated Chewing Gum Delivery System for Nicotine," the entire content of which is incorporated herein by reference. However, the nicotine replacement gum uses the nicotine replacement compositions according to embodiments of the present invention in place of the "nicotine" described in the patent document. For example, as described herein, a nicotine replacement composition for use in a nicotine replacement gum according to embodiments of the present invention may include the nicotine product described herein in addition to a gum base, polymer and/or elastomer solvent as a carrier. The nicotine replacement gum may also include a plasticizer and/or softener, a sweetener and/or flavorant, a preservative, a pH adjusting agent, and/or a filler.

In another example, a NRT product according to embodiments of the present invention includes a nicotine replacement spray (e.g., an oral spray). The nicotine replacement spray may include any of the nicotine replacement compositions according to embodiments of the present invention in a sprayable, aerosolizable, atomizable or nebulizable form. For example, the nicotine replacement composition may be a liquid composition having a viscosity suitable for forcing through an atomizer, aerosolizer, nebulizer or other spraying device.

In some examples, NRT products according to embodiments of the present invention include a nicotine replacement chewing tobacco, a nicotine replacement snuff (e.g., inhalable nicotine replacement product, such as, for example, powder) or a nicotine replacement strip (e.g., dissolvable nicotine replacement product, such as, for example, a gelatinized sheet as a mouth strip or a vaporizable film). These nicotine replacement products may include any of the nicotine replacement compositions according embodiments of the present invention embedded, impregnated, or otherwise housed in a polymeric or resinous carrier, e.g., a carrier including polymer or resin particles or fibers. The polymeric matrix housing the nicotine replacement composition may be first impregnated or embedded with the nicotine replacement composition, and then further processed to mimic the physical properties of conventional chewing tobacco, snuff or strips. For example, the resulting matrix may be cut, pulverized or otherwise mechanically processed to resemble the shape, structure, mouthfeel, texture and chew of conventional chewing tobacco, snuff or strips. Alternatively, the polymer or resin may be first processed to the desired shape, e.g., particles or fibers, and then impregnated or embedded with the nicotine replacement composition. Additionally, the polymer(s) of the matrix may be selected to mimic the chemical properties of conventional chewing tobacco, snuff or strips, such as melting or softening temperature, so that the matrix with embedded nicotine replacement composition has the same or similar mouth experience as conventional chewing tobacco, snuff or strips. Any suitable polymer or resin may be used for the polymer or resin matrix, and may differ depending on the type of NRT product. Some nonlimiting examples of polymers suitable for mimicking the properties of conventional tobacco derived chewing tobacco and/or snuff include algae-derived cellulose materials or polymers.

In addition, in some embodiments, for example, when the NRT product is a dissolvable nicotine product (e.g., a nicotine replacement strip, such as a gelatinized sheet as a mouth strip or a vaporizable film), the polymer or resin may be soluble in water and/or saliva. Any suitable non-tobacco polymer may be used for this purpose, and the dissolvable nicotine replacement product may be manufactured using techniques known in the art, as well as food-grade solvents that can be later removed by any suitable means, e.g., heat or vacuum.

In another example, a NRT product according to embodiments of the present invention includes a nicotine replacement rub, e.g., a lotion, balm, salve, oil, ointment or the like. The nicotine replacement rub may include any of the nicotine replacement compositions according to embodiments of the present invention in any form suitable for external application to a user's skin. For example, the nicotine replacement composition may be a liquid or solid composition dissolved or diluted in a carrier suitable for application to the skin, e.g., a biocompatible oil base, wax base, lotion base, balm base, salve base, ointment base or the like. The various components of external rubs (e.g., lotions, oils, balms, salves, ointments, etc.) are well known to those of ordinary skill in the art, and the skilled artisan would be readily capable of selecting appropriate components for the desired NRT product.

According to some embodiments of the present invention, a method of treating nicotine addiction comprises administering a nicotine replacement composition according to embodiments of the present invention to a user. The nicotine replacement composition may be administered via a nicotine replacement therapy product. Additionally, in some embodiments, the administration may include administering a first nicotine replacement composition having a first concentration of the nicotine product in the composition, and then administering a second nicotine replacement composition having a second concentration of the nicotine product in the composition, where the second concentration of the nicotine product is lower than the first concentration of the nicotine product. Additional administrations of additional nicotine replacement compositions with additional concentrations of the nicotine product may also be administered after administration of the second nicotine replacement composition, where each additional concentration of the nicotine becomes lower with each successive administration.

As discussed in the Examples section below, humans may have different neurophysiological responses to the R and S isomers of nicotine, and therefore different neurophysiological responses to various mixtures of the R and S isomers. The differences reported in the below Examples section in membrane receptor binding properties of the R and S isomers may also affect psychoactive neuronal pathways as well as addictive responses. Indeed, the different assay results observed in the membrane bound nicotine receptors primarily responsible for addictive response may suggest that the R isomer of nicotine can be used as an effective treatment for addiction, e.g., an effective means for smoking cessation. Additionally, given the neurophysiological differences between the R and S isomers of nicotine, a NRT product that includes all R isomer, or different levels of R isomer in the nicotine replacement composition may be used as a way to control the dose of active nicotine (i.e., S isomer). Accordingly, in some embodiments of the present invention, a method of treating nicotine addiction (or method of promoting smoking cessation) may include administering a nicotine replacement composition according to embodiments of the present invention in which at least a portion of the nicotine product includes R-Nicotine to a user. The nicotine replacement composition may be administered via a nicotine replacement therapy product. Additionally, in some embodiments, the administration may include administering a first nicotine replacement composition having a first concentration of R-isomer in the nicotine product in the composition, and then administering a second nicotine replacement composition having a second concentration of R-isomer in the nicotine product in the composition, where the second concentration of R-isomer in the nicotine product is greater than the first concentration of R-isomer in the nicotine product. Additional administrations of additional nicotine replacement compositions with additional concentrations of R-isomer in the nicotine product may also be administered after administration of the second nicotine replacement composition, where each additional concentration of R-isomer in the nicotine becomes greater with each successive administration. With such a treatment regimen of stepped increases in the amount of R isomer in the nicotine replacement compositions, the R isomer serves to control the dose of active (i.e., S isomer) nicotine.

It is understood that while some embodiments of the method of treating nicotine addiction (or the method of promoting smoking cessation) may include the administration of a composition including some R-isomer, these methods do not require the presence of R-isomer. Indeed, according to some embodiments of the present invention, the method of treating nicotine addiction (or promoting smoking cessation) includes administering a nicotine replacement composition according to embodiments of the present invention in which the nicotine product includes only S-Nicotine to a user. The nicotine replacement composition may be administered via a nicotine replacement therapy product. Additionally, in some embodiments, the administration may include administering a first nicotine replacement composition having a first concentration of S-isomer in the nicotine product in the composition, and then administering a second nicotine replacement composition having a second concentration of S-isomer in the nicotine product in the composition, where the second concentration of S-isomer in the nicotine product is lower than the first concentration of S-isomer in the nicotine product. Additional administrations of additional nicotine replacement compositions with additional concentrations of S-isomer in the nicotine product may also be administered after administration of the second nicotine replacement composition, where each additional concentration of S-isomer in the nicotine becomes lower with each successive administration. With such a treatment regimen of stepped decreases in the amount of S isomer in the nicotine replacement compositions, the increasing amount of R isomer as the treatment regimen progresses serves to control the dose of active (i.e., S isomer) nicotine.

EXAMPLES

The following Examples are provided for illustrative purposes only, and are not intended to limit the scope of any of the embodiments of the present invention.

Synthesis Example 1—R,S Nicotine Synthesis 1 equivalent of potassium hydride was added to a stirred solution of 1-vinyl-2-pyrrolidinone (2) in dry THF under a nitrogen atmosphere. The reaction mixture was stirred at room temperature for about 20 minutes, then ethyl nicotinate (1 equivalent) was added and the resulting mixture was stirred for 24 hours at 65 degrees centigrade. The reaction was cooled and then acidified with 5% HCl, and then concentrated HCl was added and the resulting solution was refluxed for 48 hours. The pH was adjusted to 13 with sodium hydroxide, and the aqueous and organic layers of the resulting biphasic solution were separated three times using equal volumes of dichloromethane. The combined extracts from the separation were dried over sodium sulfate, filtered and the solvent evaporated to give an amorphous material. The amorphous material was taken up in 3 parts ethanol, and then palladium-on-carbon was added (about 10%) and the resulting mixture was subjected to hydrogen pressure for 6 hours (greater than 25 atmospheres). The resulting residue was diluted with more ethanol and filtered through celite. The solvent was evaporated to dryness under vacuum with minimal heat, and then the residue was taken up in a formic acid/formaldehyde solution (1:1). The resulting mixture was heated to an internal temperature of 90 degrees Celsius and maintained at this temperature over a period of 12 hours, and then cooled and neutralized with sodium hydroxide to a pH of greater than 10, and then extracted with dichloromethane and dried over sodium sulfate, filtered and concentrated to give a brown oil. This oil was vacuum distilled to give pure RS Nicotine.

Synthesis Example 2—R,S Nicotine Synthesis 1.2 equivalent of sodium hydride was added to a stirred solution of 1-vinyl-2-pyrrolidinone (2) in dry THF/DMF (3/1) under a nitrogen atmosphere. The reaction mixture was stirred at room temperature for about 20 minutes, then ethyl nicotinate (1 equivalent) was added, and the resulting mixture was stirred for 24 hours at 65 degrees centigrade. The reaction was cooled and then acidified with 5% HCl, and then concentrated HCl was added, and the resulting mixture was refluxed for 48 hours. The pH was adjusted to 6 with sodium hydroxide, and then excess dichloromethane was added and the layers were separated. The aqueous layer was extracted twice with excess dichloromethane, and the extracts were combined and washed with water, and then dried over sodium sulfate. The solution was then filtered and the solvent removed using vacuum to yield a brownish solid. This solid was dissolved in ethanol (about 5 to about 10 parts), and then 0.5 parts palladium on carbon was added and the resulting mixture was subjected to hydrogen pressure for 6 hours (greater than 25 atmospheres). The resulting residue was diluted with more ethanol and filtered through celite. The solvent was evaporated to dryness under vacuum with minimal heat, and then the residue was taken up in 3 parts formic acid and 3 parts formaldehyde, and the resulting solution was heated to an internal temperature of about 90 to about 95 degrees centigrade and maintained at this temperature over a period of 24 hours. The reaction was cooled and then vacuum distilled to yield pure RS nicotine as a clear, colorless non-viscous oil.

Synthesis Example 3—R,S Nicotine Synthesis 1 equivalent of potassium hydride was added to a stirred solution of 1-vinyl-2-pyrrolidinone (2) in dry DMF under a nitrogen atmosphere. The reaction mixture was stirred at room temperature for about 20 minutes, then ethyl nicotinate (1 equivalent) was added and the resulting mixture was stirred for 24 hours at 65 degrees centigrade. The reaction was cooled and then acidified with 5% HCl and then refluxed for 48 hours. The pH was adjusted to 6 with sodium hydroxide, and then a suspension of sodium borohydride in isopropanol was added in excess and the reaction mixture was stirred for 24 hours at room temperature. The reaction mixture was then acidified to a pH of about 3 with 5% HCl, and then stirred for about 15 minutes. 10 parts dichloromethane was added and the layers were separated. The organic layer was dried over sodium sulfate and filtered, and then 1.1 equivalents of potassium carbonate was added, and then 1.1 equivalents of methyl iodide was added and the reaction mixture was stirred for 24 hours and filtered, and the solvent was removed to yield an oil which was vacuum distilled to yield pure RS nicotine.

Synthesis Example 4—R,S Nicotine Synthesis 1 equivalent of potassium hydride was added to a stirred solution of 1-vinyl-2-pyrrolidinone (2) in dry THF under a nitrogen atmosphere. The reaction mixture was stirred at room temperature for about 20 minutes, then ethyl nicotinate (1 equivalent) was added and the resulting mixture was stirred for 24 hours at 65 degrees centigrade. The reaction was cooled and then acidified with 5% HCl and then concentrated HCl was added and the resulting mixture was refluxed for 48 hours. The pH was adjusted to 6 with sodium hydroxide, and then a suspension of sodium borohydride in isopropanol was added in excess and the reaction mixture was stirred for 24 hours at room temperature. About 10 parts formic acid and about 10 parts formaldehyde were then added, and the resulting solution was stirred at about 100 degrees centigrade for 24 hours, cooled, and then brought to a pH of about 12 by addition of a sodium hydroxide solution. The layers were then separated and the aqueous layer was washed many times with dichloromethane. The organic extracts were dried over sodium sulfate and the solvent was removed. The resulting crude oil was vacuum distilled to yield pure RS nicotine as a clear and colorless non viscous liquor.

Synthesis Example 5—R,S Nicotine Synthesis 1.2 equivalents of sodium hydride (60% dispersion in oil) was added to a stirred solution of 1-vinyl-2-pyrrolidinone (2) in toluene, and then a concentrated solution of ethyl nicotinate (1 equivalent) in toluene was added drop-wise over 20 min. The resulting mixture was heated to reflux for 3 hours. This crude reaction mixture was cooled in an ice bath, and then excess concentrated hydrochloric acid was added and the resulting solution was heated to an internal temperature of about 85 to about 110 degrees Celsius and maintained at this temperature over a period of 12 hours. The reaction mixture was then cooled to room temperature, and the upper toluene layer removed. Sodium hydroxide was added to the acidic aqueous layer until the pH was greater than 12, and then the pH was adjusted to about 8 with HCl. 2.5 equivalents of sodium borohydride solution in isopropanol (stabilized with sodium hydroxide) were added to the stirred solution, and the resulting mixture was stirred for 6 hours (until the reaction was completed). Excess formic acid and formaldehyde was then added, and the resulting mixture was refluxed for 10 hours, and then brought to neutral or slightly basic pH with sodium hydroxide, and then the solvents were removed by vacuum and the remaining residue was vacuumed distilled to yield pure R,S, Nicotine (boiling point=74 to 76 degrees Celsius @ 0.5 mmHg).

Synthesis Example 6—Myosamine Synthesis

Sodium hydride (1.25 Kg, 31.2 mole) was added to a stirred solution of toluene (10 L) in an inert atmosphere (dry nitrogen or argon gas) and stirred for about 15 minutes at room temperature. Then, a solution of n-vinyl pyrrolidinone (2 kg, 18.02 mole) in 1 L of toluene was added over 15 minutes via funnel addition, and the resulting mixture was stirred at ambient temperature for about 15 minutes. Then, a solution of ethyl nicotinate (2.5 Kg, 16.56 mole) in 2 L toluene was added in portions over a two hour period. The mildly effervescent exothermic reaction mixture turned a light rose color and then a light green precipitant formed as the exothermic reaction maintained itself at about 60 to about 65° C. After the addition was complete, the reaction mixture was heated to an internal temperature of about 85° C. and maintained at this temperature for about 16 hours, then cooled to room temperature yielding a greenish heterogeneous mixture. This greenish heterogeneous mixture flows well and can be pumped through a ½ polyethylene tubing using a diaphragm pump. The greenish heterogeneous mixture was added, in about 250 mL portions, to 25 L of a boiling solution of 6N HCl. The addition took place with vigorous effervescence, which subsided within a few minutes after addition of the aliquot of the reaction mixture to the hot HCl. After all the reaction mixture was added, the resulting dark brown biphasic mixture was stirred under reflux for an additional hour. Then, the reaction mixture was cooled, and the layers were separated. The aqueous layer was cooled, made basic (i.e., having a pH greater than 10) using NaOH (50%), and then extracted 3 times with 8 L of dichloromethane. The solvent was then removed via vacuum distillation (temperature of the bath was about 45 degrees centigrade) to yield crude myosamine as a dark brown, non-viscous oil.

Synthesis Example 7—Nornicotine Synthesis

The total crude myosamine from Synthesis Example 6 was taken up in 16 L of ethanol. 250 grams of 10% palladium-on-carbon was added, and the resulting mixture was stirred in a hydrogen atmosphere for 12 hours, followed by filtering using celite, and washing with ethanol. The ethanol was removed by vacuum to give crude nornicotine as a dark brown non-viscous oil.

Synthesis Example 8—R,S Nicotine Synthesis 2.0 Kg of formaldehyde (37%) and 1.5 Kg of formic acid (85%) were added to the crude nornicotine from Synthesis Example 7. The resulting brown solution was heated to an internal temperature of 85 degrees centigrade and maintained at this temperature for 15 hours, and then cooled to ambient temperature. The resulting solution was chilled to about 5 degrees centigrade, and then made basic by addition of NaOH. The resulting solution was then extracted 3 times with 8 L of dichloromethane, and the solvent was removed by vacuum. Pure R,S-nicotine was obtained using high vacuum distillation (i.e., 75 to 76 @ 0.5 mmHg) to yield a clear, colorless non-viscous oil (about 31% overall yield from ethyl nicotinate).

Synthesis Example 9—Synthesis of Nornicotine

The total crude myosamine from Synthesis Example 6 was taken up in 16 L methanol and 4 L of acetic acid. The resulting solution was cooled to an internal temperature of −40 degrees centigrade, and then 700 grams of sodium borohydride (granular) was added in portions over 1 hour. The reaction mixture was allowed to warm to room temperature with stirring, and was then submitted to vacuum distillation to remove most of the solvent. The resulting liquor was added to 25 L of water, and the resulting solution was brought to a pH greater than 10 with NaOH. The resulting solution was extracted three times with 15 L of dichloromethane, and the combined extracts were subjected to medium vacuum distillation to give crude nornicotine as a crude non-viscous dark brown colored oil.

Synthesis Example 10—Synthesis of R,S Nicotine

A solution of N-vinyl pyrrolidinone (4.5 kg) in 2.5 Kg of toluene was added to 2.5 Kg of Sodium Hydride (60% dispersion in mineral oil) as a stirred suspension in 20 L of toluene. The resulting mixture was stirred for about 15 minutes at room temperature. 5 Kg of ethyl nicotinate in 10 Kg of toluene was added to the resulting mixture in portions and by a constant slow stream of liquor (light golden color). The exothermic reaction was controlled at an internal temperature of about 60° C. by controlling the rate of addition of the ethyl nicotinate-toluene solution. After addition of about one third of the ethyl nicotinate, a green precipitate was formed. After addition was completed, the green heterogeneous mixture was heated to an internal temperature of about 85° C. and maintained at this temperature for about 12 hours. The resulting solution was injected into a precooled solution of 30 L of 4N HCl at 0° C. followed by vigorous stirring for about 5 minutes. The layers were separated, and the toluene layer was washed once with 2.5 Kg of 4N HCl. 8 L of concentrated HCl was added to the combined acidic aqueous layers, and the reaction mixture was heated to boiling and maintained at this temperature for about 3 hours (or until the reaction was completed, as determined by thin layer chromatography (TLC)). The reaction mixture was cooled to 0° C., and then neutralized with 50% sodium hydroxide solution while not allowing the internal temperature to go above 35 to 40 degrees centigrade. The pH was made very basic by addition of a sodium hydroxide solution (50%) until the pH reached 11 to 13 (as indicated by a blue color change on litmus paper). The resulting solution was extracted 4 times with 15 L of dichloromethane, and the combined extracts were subjected to medium vacuum distillation to yield myosamine as a non-viscous brownish oil.

40 L of anhydrous ethanol was added to the crude myosamine product, and the resulting solution was added to 2 Kg of 10% palladium-on-carbon. The resulting mixture was subjected to hydrogen pressure of 50 atm. The reaction was completed within 12 hours. The resulting heterogeneous mixture was filtered through celite, and then washed twice with 10 L of ethanol. The combined ethanolic solutions of the crude nornicotine product was subjected to vacuum distillation (29 inches Hg) at below 50° C., and then the crude dark brown oil was taken up in 10 L water. A solution of 5 L of formaldehyde solution (37%) with 4 L of formic acid (85%) was added to the resulting solution, and the mixture was heated to an internal temperature of 90° C. and maintained at this temperature for 20 hours. The reaction mixture was cooled to −5° C., and then made basic (i.e., a pH greater than 10) by addition of a sodium hydroxide solution (50%). The basic liquor was then extracted 3 times with 15 L of dichloromethane, and the combined extracts were subjected to med vacuum distillation to yield crude RS-Nicotine product as a dark brown oil. The dark brown oil was high vacuum distilled twice to yield RS-Nicotine having a purity that meets the requirements of the USP purity test.

In a study of the differences between synthetic nicotine according to embodiments of the present invention and tobacco-derived nicotine, electrophysiology-based HTS assay was used to evaluate and compare the activity of different nicotine forms on two nicotinic ACh receptors (nAChRs), i.e., α7 and α4β2. The nicotinic forms subjected to this assay included an S nicotine available from Sigma-Aldrich Corporation, St. Louis, Mo., a synthetic RS racemic mixture of R and S isomers according to embodiments of the present invention, a synthetic S nicotine according to embodiments of the present invention, a synthetic RS mixture including 75% S and 25% R isomers according to embodiments of the present invention, a synthetic R nicotine according to embodiments of the present invention, a synthetic RS mixture including 25% S and 75% R isomers according to embodiments of the present invention, an S nicotine available from Alchem Laboratories Corporation, Alachua, Fla., and a reference nicotine available from Sigma-Aldrich. The results of the assay are provided in Tables 1 and 2 below, which show the obtained $EC_{50}$, $IC_{50}$, $E_{max}$ and Hillslope values of receptor activation and inhibition.

TABLE 1

α4β2 nAChRs activation and inhibition

| Composition | Agonist Effect | | | Antagonist Effect | |
|---|---|---|---|---|---|
| | Emax, % | EC50, μM | Hillslope | IC50, μM | Hillslope |
| Sigma-Aldrich S nicotine | 91 | 3.11 | −0.84 | 0.01 | 0.94 |
| Synthetic RS racemic nicotine | 96 | 9.91 | −0.77 | 0.03 | 1.27 |
| Synthetic S nicotine | 91 | 3.54 | −0.88 | 0.01 | 0.93 |
| Synthetic 75% S/25% R nicotine | 99 | 5.15 | −0.76 | 0.02 | 1.04 |
| Synthetic R nicotine | 28 | 10.79 | −0.87 | 0.14 | 0.67 |
| Synthetic 25% S/75% R nicotine | 80 | 9.30 | −0.90 | 0.04 | 1.11 |
| Alchem S nicotine | 103 | 3.71 | −0.81 | 0.01 | 1.01 |
| Ref. nicotine (Sigma-Aldrich) | 100 | 4.13 | −0.80 | 0.01 | 0.85 |

TABLE 2

α7 nAChRs activation and inhibition

| Composition | Agonist Effect | | | Antagonist Effect | |
|---|---|---|---|---|---|
| | Emax, % | EC50, μM | Hillslope | IC50, μM | Hillslope |
| Sigma-Aldrich S nicotine | 104 | 1.20 | −2.49 | 0.80 | 2.76 |
| Synthetic RS racemic nicotine | 108 | 2.07 | −1.97 | 1.20 | 3.38 |
| Synthetic S nicotine | 102 | 1.07 | −3.36 | 0.84 | 5.83 |
| Synthetic 75% S/25% R nicotine | 102 | 1.39 | −2.64 | 0.99 | 5.16 |
| Synthetic R nicotine | 110 | 5.81 | −2.37 | 4.07 | 2.55 |
| Synthetic 25% S/75% R nicotine | 105 | 2.69 | −2.35 | 2.39 | 4.70 |
| Alchem S nicotine | 97 | 1.00 | −3.15 | 0.73 | 3.06 |
| Ref. nicotine (Sigma-Aldrich) | 100 | 1.21 | −2.23 | 0.92 | 10.02 |

As can be seen in the above Tables 1 and 2, the synthetic R nicotine according to embodiments of the present invention appears to be a full, weak agonist at human α7 nAChRs, but only a partial agonist at human α4β2 nAChRs, suggesting a selectivity of the nicotine isomers at different types of nAChRs, which is surprising and unexpected. For example, these results may suggest different neurophysiological responses to the R and S isomers of nicotine, and therefore different neurophysiological responses to various mixtures of the R and S isomers. These differences in the neurophysiological response may be responsible for the different sensory experiences reported in Tables 1 and 2 above, and these differences in membrane receptor binding properties of the R and S isomers may also affect psychoactive neuronal pathways as well as addictive responses.

In a second study of the differences between synthetic nicotine according to embodiments of the present invention and tobacco-derived nicotine, electrophysiology-based HTS assay was used to evaluate and compare the activity of different nicotine forms on two additional nicotinic ACh receptors (nAChRs), i.e., α6/3β2β3 and α3β4α5. The nicotinic forms subjected to this assay included an S nicotine available from Sigma-Aldrich Corporation, St. Louis, Mo., a synthetic RS racemic mixture of R and S isomers according to embodiments of the present invention, a synthetic S nicotine according to embodiments of the present invention, a synthetic RS mixture including 75% S and 25% R isomers according to embodiments of the present invention, a synthetic R nicotine according to embodiments of the present invention, a synthetic RS mixture including 25% S and 75% R isomers according to embodiments of the present invention, an S nicotine available from Alchem Laboratories Corporation, Alachua, Fla., and a reference nicotine available from Sigma-Aldrich. The results of the assay are provided in Tables 3 and 4 below, which show the obtained $EC_{50}$, $IC_{50}$, $E_{max}$ and Hillslope values of receptor activation and inhibition.

TABLE 3

α6/3β2β3 nAChRs activation and inhibition

| Composition | Agonist Effect | | | Antagonist Effect | |
|---|---|---|---|---|---|
| | Emax, % | EC50, μM | Hillslope | IC50, μM | Hillslope |
| Sigma-Aldrich S nicotine | 100 | 1.23 | −0.69 | 0.02 | 0.96 |
| Synthetic RS racemic nicotine | 91 | 3.56 | −0.67 | 0.03 | 1.36 |
| Synthetic S nicotine | 97 | 0.94 | −0.70 | 0.01 | 1.10 |
| Synthetic 75% S/25% R nicotine | 103 | 2.28 | −0.65 | 0.01 | 0.68 |
| Synthetic R nicotine | 70 | 3.87 | −0.92 | 0.10 | 1.07 |
| Synthetic 25% S/75% R nicotine | 94 | 3.39 | −0.75 | 0.01 | 0.62 |

TABLE 3-continued

α6/3β2β3 nAChRs activation and inhibition

| | Agonist Effect | | | Antagonist Effect | |
|---|---|---|---|---|---|
| Composition | Emax, % | EC50, μM | Hillslope | IC50, μM | Hillslope |
| Alchem S nicotine | 95 | 1.27 | −0.81 | 0.01 | 0.97 |
| Ref. nicotine (Sigma-Aldrich) | 100 | 1.20 | −0.74 | 0.0057 | 0.72 |

TABLE 4

α3β4α5 nAChRs activation and inhibition

| | Agonist Effect | | | Antagonist Effect | |
|---|---|---|---|---|---|
| Composition | Emax, % | EC50, μM | Hillslope | IC50, μM | Hillslope |
| Sigma-Aldrich S nicotine | 84 | 28.63 | −1.91 | 0.26 | 1.38 |
| Synthetic RS racemic nicotine | 65 | 32.30 | −2.13 | 0.44 | 1.52 |
| Synthetic S nicotine | 96 | 28.57 | −1.48 | 0.27 | 1.11 |
| Synthetic 75% S/25% R nicotine | 96 | 42.25 | −1.65 | 0.44 | 1.65 |
| Synthetic R nicotine | 21 | 54.28 | −2.37 | 2.54 | 0.95 |
| Synthetic 25% S/75% R nicotine | 51 | 41.31 | −1.97 | 0.82 | 1.17 |
| Alchem S nicotine | 87 | 29.26 | −1.46 | 0.33 | 1.34 |
| Ref. nicotine (Sigma-Aldrich) | 100 | 29.22 | −1.48 | 0.3004 | 1.59 |

As can be seen in the above Tables 3 and 4, the synthetic R nicotine according to embodiments of the present invention appears to be a full, weak agonist at human α6/3β2β3 nAChRs, but only a partial, weak agonist at human α3β4α5 nAChRs, suggesting a selectivity of the nicotine isomers at different types of nAChRs, which is surprising and unexpected. For example, like the results discussed above for the α7 and α4β2 nAChRs, these results may suggest different neurophysiological responses to the R and S isomers of nicotine, and therefore different neurophysiological responses to various mixtures of the R and S isomers. As discussed above in connection with the results for the α7 and α4β2 nAChRs, these differences in the neurophysiological response may be responsible for the different sensory experiences, and these differences in membrane receptor binding properties of the R and S isomers may also affect psycho-active neuronal pathways as well as addictive responses.

As discussed above, nicotine replacement compositions according to embodiments of the present invention include a synthetic nicotine source that improves the sensory experience, while also providing certain health and economic benefits. For example, while natural or tobacco derived nicotine typically has a foul taste, and is malodorous and carcinogenic, the nicotine replacement compositions according to embodiments of the present invention are non-carcinogenic and do not have the foul taste and smell characteristic of tobacco derived nicotine.

Also, because tobacco-derived nicotine compositions typically include contaminants that are the byproducts of extraction from tobacco leaves, these compositions may spoil sooner than the nicotine replacement compositions according to embodiments of the present invention incorporating synthetic nicotine sources. Indeed, nicotine replacement compositions according to embodiments of the present invention have improved shelf life or shelf stability than their tobacco-derived or natural counterparts.

Additionally, while tobacco-derived nicotine compositions for certain applications typically include large amounts of sweeteners and flavorants to mask the foul taste of the tobacco-derived nicotine, the nicotine replacement compositions according to embodiments of the present invention need not use so much sweetener and/or flavorant. As discussed above, this reduction in the amount of sweetener and/or flavorant can improve the sensory experience and decrease the health consequences typically associated with tobacco derived nicotine.

While certain exemplary embodiments of the present disclosure have been illustrated and described, those of ordinary skill in the art will recognize that various changes and modifications can be made to the described embodiments without departing from the spirit and scope of the present invention, and equivalents thereof, as defined in the claims that follow this description. For example, although certain components may have been described in the singular, i.e., "a" flavorant, "a" solvent, and the like, one or more of these components in any combination can be used according to the present disclosure.

Also, although certain embodiments have been described as "comprising" or "including" the specified components, embodiments "consisting essentially of" or "consisting of" the listed components are also within the scope of this disclosure. For example, while embodiments of the present invention are described as including a nicotine source that comprises a synthetic nicotine, a nicotine source consisting essentially of or consisting of a synthetic nicotine is also within the scope of this disclosure. Accordingly, the nicotine source may consist essentially of the synthetic nicotine. In this context, "consisting essentially of" means that any additional components in the nicotine source will not materially affect the user experience in terms of taste or neurological effect. For example, a nicotine source consisting essentially of the synthetic nicotine may exclude any measurable or detectable amount of the contaminants or impurities described herein as normally associated with tobacco-derived nicotine.

As used herein, unless otherwise expressly specified, all numbers such as those expressing values, ranges, amounts or percentages may be read as if prefaced by the word "about," even if the term does not expressly appear. Further, the word "about" is used as a term of approximation, and not as a term of degree, and reflects the penumbra of variation associated with measurement, significant figures, and interchangeability, all as understood by a person having ordinary skill in the art to which this disclosure pertains. Any numerical range recited herein is intended to include all sub-ranges subsumed therein. Plural encompasses singular and vice versa. For example, while the present disclosure may describe "a" flavorant or "a" solvent, a mixture of such flavorants or solvents can be used. When ranges are given, any endpoints of those ranges and/or numbers within those ranges can be combined within the scope of the present disclosure. The terms "including" and like terms mean "including but not limited to," unless specified to the contrary.

Notwithstanding that the numerical ranges and parameters set forth herein may be approximations, numerical values set forth in the Examples are reported as precisely as is practical. Any numerical value, however, inherently contains certain errors necessarily resulting from the standard variation found in their respective testing measurements. The word "comprising" and variations thereof as used in this description and in the claims do not limit the disclosure to exclude any variants or additions.

What is claimed is:

1. A method of treating nicotine addiction, the method comprising:
    administering to a subject with nicotine addiction a first nicotine replacement composition, the first nicotine replacement composition comprising:
        a first nicotine product comprising a first synthetic nicotine substantially free of one or more of nicotine-1'-N-oxide, nicotyrine, nornicotyrine, cotinine, 2',3-bipyridyl, anabasine, N-methyl anatabine, N-methyl anabasine, and/or anatabine, the first synthetic nicotine comprising a first ratio of (R)-nicotine to (S)-nicotine, and
        one or more first pharmaceutically acceptable excipients, additives and/or carriers; and
    subsequent to administering the first nicotine replacement composition, administering to the subject a second nicotine replacement composition, the second nicotine replacement composition comprising:
        a second nicotine product comprising a second synthetic nicotine substantially free of one or more of nicotine-1'-N-oxide, nicotyrine, nornicotyrine, cotinine, 2',3-bipyridyl, anabasine, N-methyl anatabine, N-methyl anabasine, and/or anatabine, the second synthetic nicotine product comprising a second ratio of (R)-nicotine to (S)-nicotine, the second ratio of (R)-nicotine to (S)-nicotine being different from the first ratio of (R)-nicotine to (S)-nicotine, and the second ratio of (R)-nicotine to (S)-nicotine having more (R)-nicotine than the first ratio of (R)-nicotine to (S) nicotine, and
        one or more second pharmaceutically acceptable excipients, additives and/or carriers.

2. The method of treating nicotine addiction according to claim 1, wherein the first ratio of (R)-nicotine to (S)-nicotine has more (S)-nicotine than (R)-nicotine.

3. The method of treating nicotine addiction according to claim 1, wherein the first ratio of (R)-nicotine to (S)-nicotine is 0:100.

4. The method of treating nicotine addiction according to claim 1, wherein the second ratio of (R)-nicotine to (S)-nicotine has more (R)-nicotine than (S)-nicotine.

5. The method of treating nicotine addiction according to claim 1, wherein the second ratio of (R)-nicotine to (S)-nicotine is 100:0.

6. The method of treating nicotine addiction according to claim 1, further comprising:
    subsequent to administering the second nicotine replacement composition, administering to the subject one or more additional nicotine replacement composition, each of the one or more additional nicotine replacement compositions comprising:
        a respective nicotine product comprising a respective synthetic nicotine substantially free of one or more of nicotine-1'-N-oxide, nicotyrine, nornicotyrine, cotinine, 2',3-bipyridyl, anabasine, N-methyl anatabine, N-methyl anabasine, and/or anatabine, each respective synthetic nicotine product comprising a respective ratio of (R)-nicotine to (S)-nicotine, each respective ratio of (R)-nicotine to (S)-nicotine being different from the first ratio of (R)-nicotine to (S)-nicotine and the second ratio of (R)-nicotine to (S)-nicotine, and each respective ratio of (R)-nicotine to (S)-nicotine having more (R)-nicotine than the first ratio of (R)-nicotine to (S) nicotine, the second ratio of (R)-nicotine to (S)-nicotine, and each other respective ratio of (R)-nicotine to (S)-nicotine that is administered earlier, and
        one or more respective pharmaceutically acceptable excipients, additives and/or carriers.

7. The method of treating nicotine addiction according to claim 6, wherein the first ratio of (R)-nicotine to (S)-nicotine has more (S)-nicotine than (R)-nicotine.

8. The method of treating nicotine addiction according to claim 6, wherein the first ratio of (R)-nicotine to (S)-nicotine is 0:100.

9. The method of treating nicotine addiction according to claim 6, wherein the respective ratio of (R)-nicotine to (S)-nicotine in the respective nicotine product of a final one of the one or more additional nicotine replacement compositions has more (R)-nicotine than (S)-nicotine.

10. The method of treating nicotine addiction according to claim 6, wherein the respective ratio of (R)-nicotine to (S)-nicotine in the respective nicotine product of a final one of the one or more additional nicotine replacement compositions is 100:0.

11. A method of treating nicotine addiction, the method comprising:
    administering to a subject with nicotine addiction a first nicotine replacement composition, the first nicotine replacement composition comprising:
        a first nicotine product comprising a first synthetic nicotine substantially free of one or more of nicotine-1'-N-oxide, nicotyrine, nornicotyrine, cotinine, 2',3-bipyridyl, anabasine, N-methyl anatabine, N-methyl anabasine, and/or anatabine, the first synthetic nicotine comprising a first ratio of (R)-nicotine to (S)-nicotine, and
        one or more first pharmaceutically acceptable excipients, additives and/or carriers; and
    subsequent to administering the first nicotine replacement composition, administering to the subject one or more additional nicotine replacement compositions, each of the one or more additional nicotine replacement compositions comprising:

a respective nicotine product comprising a respective synthetic nicotine substantially free of one or more of nicotine-1'-N-oxide, nicotyrine, nornicotyrine, cotinine, 2',3-bipyridyl, anabasine, N-methyl anatabine, N-methyl anabasine, and/or anatabine, each respective synthetic nicotine product comprising a respective ratio of (R)-nicotine to (S)-nicotine, each respective ratio of (R)-nicotine to (S)-nicotine being different from the first ratio of (R)-nicotine to (S)-nicotine, and each respective ratio of (R)-nicotine to (S)-nicotine having more (R)-nicotine than the first ratio of (R)-nicotine to (S) nicotine and having more (R)-nicotine than each other respective ratio of (R)-nicotine to (S)-nicotine that is administered earlier, and one or more respective second pharmaceutically acceptable excipients, additives and/or carriers.

12. The method of treating nicotine addiction according to claim 11, wherein the first ratio of (R)-nicotine to (S)-nicotine has more (S)-nicotine than (R)-nicotine.

13. The method of treating nicotine addiction according to claim 11, wherein the first ratio of (R)-nicotine to (S)-nicotine is 0:100.

14. The method of treating nicotine addiction according to claim 11, wherein the respective ratio of (R)-nicotine to (S)-nicotine in the respective nicotine product of a final one of the one or more additional nicotine replacement compositions has more (R)-nicotine than (S)-nicotine.

15. The method of treating nicotine addiction according to claim 11, wherein the respective ratio of (R)-nicotine to (S)-nicotine in the respective nicotine product of a final one of the one or more additional nicotine replacement compositions is 100:0.

16. A method of treating nicotine addiction, the method comprising:

administering to a subject with nicotine addiction a plurality of different nicotine replacement compositions over time, each of the different nicotine replacement compositions comprising:

a respective nicotine product comprising a respective synthetic nicotine substantially free of one or more of nicotine-1'-N-oxide, nicotyrine, nornicotyrine, cotinine, 2',3-bipyridyl, anabasine, N-methyl anatabine, N-methyl anabasine, and/or anatabine, each of the respective synthetic nicotines comprising a different ratio of an amount of (R)-nicotine to an amount of (S)-nicotine, each of the plurality of different nicotine replacement compositions being administered at a different time during the method of treating the nicotine addiction such that the administering the plurality of different nicotine replacement compositions over time results in a stepped increase in the amount of (R)-nicotine and a stepped decrease in the amount of (S)-nicotine over time; and one or more pharmaceutically acceptable excipients, additives and/or carriers.

17. The method of treating nicotine addiction according to claim 16, wherein the ratio of the amount of (R)-nicotine to the amount of (S)-nicotine in a first one of the plurality of different nicotine replacement compositions has more (S)-nicotine than (R)-nicotine.

18. The method of treating nicotine addiction according to claim 16, wherein the ratio of the amount of (R)-nicotine to the amount of (S)-nicotine in a first one of the plurality of different nicotine replacement compositions is 0:100.

19. The method of treating nicotine addiction according to claim 16, wherein the ratio of the amount of (R)-nicotine to the amount of (S)-nicotine in a final one of the plurality of different nicotine replacement compositions has more (R)-nicotine than (S)-nicotine.

20. The method of treating nicotine addiction according to claim 16, wherein the ratio of the amount of (R)-nicotine to the amount of (S)-nicotine in a final one of the plurality of different nicotine replacement compositions is 100:0.

\* \* \* \* \*